United States Patent [19]

Saito et al.

[11] Patent Number: 5,164,112
[45] Date of Patent: Nov. 17, 1992

[54] α-HYDROXYKETONE DERIVATIVES, LIQUID CRYSTAL COMPOSITIONS CONTAINING SAID DERIVATIVES, AND LIQUID CRYSTAL DEVICES USING SAID COMPOSITIONS

[75] Inventors: Shinichi Saito; Hiromichi Inoue; Kouji Ohno, all of Chibaken, Japan

[73] Assignee: Chisso Corporation, Osaka, Japan

[21] Appl. No.: 553,957

[22] Filed: Jul. 17, 1990

[30] Foreign Application Priority Data

Jul. 21, 1989 [JP] Japan ................. 1-190239

[51] Int. Cl.$^5$ ................ C09K 19/06; C09K 19/12; C07C 207/00; C07D 211/70
[52] U.S. Cl. ............. 252/299.6; 252/299.63; 252/299.61; 252/299.66; 252/299.67; 252/299.65; 568/305; 568/306; 568/307; 568/308; 568/335; 560/64; 560/102; 546/339; 546/342
[58] Field of Search ............. 560/64, 102; 568/335, 568/308, 325, 305, 306, 307; 252/299.65, 299.61, 299.63, 299.66, 299.67; 546/339, 342; 544/298

[56] References Cited

U.S. PATENT DOCUMENTS

| | | | |
|---|---|---|---|
| 4,668,427 | 5/1987 | Saito et al. | 252/299.66 |
| 4,725,688 | 2/1988 | Taguchi et al. | 544/298 |
| 4,775,223 | 10/1988 | Yoshinaga et al. | 350/333 |
| 4,818,432 | 4/1989 | Miyazawa et al. | 252/299.66 |
| 4,882,083 | 11/1989 | Terashima et al. | 252/299.61 |
| 4,886,623 | 12/1989 | Mitsuhashi | 252/299.65 |
| 4,961,875 | 10/1990 | Ohno et al. | 252/299.66 |
| 4,970,023 | 11/1990 | Hirai et al. | 252/299.66 |
| 4,973,426 | 11/1990 | Ohno et al. | 252/299.66 |
| 5,049,308 | 9/1991 | Mitsuhashi et al. | 252/299.67 |

FOREIGN PATENT DOCUMENTS 1-311051 12/1989 Japan .

Primary Examiner—Robert L. Stoll
Assistant Examiner—C. Harris
Attorney, Agent, or Firm—Wenderoth, Lind & Ponack

[57] ABSTRACT

α-hydroxyketone derivatives represented by the general formula (I) which are novel optically active compounds; liquid crystal compositions, such as chiral smectic or chiral nematic compositions, containing the derivatives; and liquid crystal devices using the compositions.

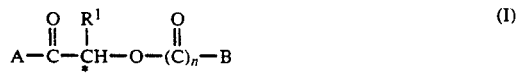

wherein A and B are independently a radical represented by the general formula (II):

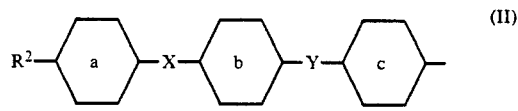

wherein $R^2$ is an aliphatic hydrocarbon having 1 to 16 carbon atoms, which may contain —O— and may be substituted by a cyano group and/or a halogen atom,

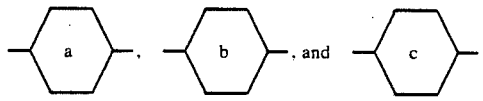

are independently a single bond,

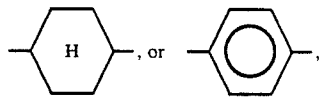

etc., X and Y are independently a single bond, or —CH$_2$CH$_2$—, etc., or an aliphatic hydrocarbon having 1 to 16 carbon atoms; $R^1$ is an alkyl group, a phenyl group, or a cyclohexyl group; n is 0 or 1; and the asterisk (*) indicates an asymmetric carbon atom.

14 Claims, No Drawings

α-HYDROXYKETONE DERIVATIVES, LIQUID CRYSTAL COMPOSITIONS CONTAINING SAID DERIVATIVES, AND LIQUID CRYSTAL DEVICES USING SAID COMPOSITIONS

FIELD OF THE INVENTION

The present invention relates to α-hydroxyketone derivatives, liquid crystal compositions containing the derivatives, and electro-optic devices (herein referred to as "liquid crystal devices") using the compositions. More particularly, it is concerned with α-hydroxyketone derivatives which are novel optically active substances, and induce ferroelectricity and further induce a helical structure in nematic and smectic liquid crystal compositions; chiral smectic or chiral nematic liquid crystal compositions containing the derivatives; and liquid crystal devices using the liquid crystal compositions.

BACKGROUND OF THE INVENTION

At the present time, as liquid crystal displays, displays of twisted nematic (TN) mode (hereinafter referred to as "TN displays") are most widely used. These TN displays have a number of advantages such as low driving voltage, and low electric power consumption. However, they are markedly inferior in response speed to emissive type displays such as cathode ray tubes, electroluminescence displays, and plasma displays.

Although new type TN displays in which a tilt angle of liquid crystal molecules is set to 180° to 270° have been developed, they are still inferior in response speed to the emissive type displays.

Although various attempts have been made to improve the response speed of TN displays, a TN display exhibiting a quick response has not been developed.

On the other hand, a new display mode using ferroelectric liquid crystals which are now under extensive investigation is expected to be greatly improved in response speed (N. Clark et al., Applied Phys. Lett., 36, 899 (1980)). This display mode utilizes a chiral smectic phase, such as a chiral smectic C phase (Sc*), exhibiting ferroelectric properties. As well as the above chiral smectic C phase, chiral smectic F, G, H, and I phases exhibit ferroelectric properties.

A number of characteristics are required for a ferroelectric liquid crystal material to be used in a ferroelectric liquid crystal device. Typical examples of such characteristics are spontaneous polarization (Ps), a tilt angle ($\theta$), viscosity ($\eta$), liquid crystal sequence, and so forth.

Among response time ($\tau$), Ps, and $\eta$, there is the following relation:

$$\tau \propto \frac{\eta}{Ps}.$$

Thus, in order to obtain quick response, it is necessary that Ps be large, and $\eta$ be small.

Further, two types of ferroelectric liquid crystal display modes are mainly employed for a ferroelectric liquid crystal display device. One is a birefringence mode using a pair of polarizers, and the other is a guest-host mode using one polarizer and a liquid crystal composition containing dichroic dye. In order to obtain the highest contrast ratio in these display modes, the tilt angles should be 22.5° and 45° in the birefringence mode and the guest-host mode, respectively.

At the present time, however, a compound capable of satisfying the above requirements by itself cannot be found. Thus, ferroelectric liquid crystal compositions comprising a plurality of liquid crystal compounds, or liquid crystal compounds and mesogenic compounds have been proposed as liquid crystal materials for use in ferroelectric liquid crystal displays.

More specifically, there have been proposed: (a) a composition consisting only of ferroelectric liquid crystal compounds; and (b) a composition which comprises a compound exhibiting a non-chiral, tilted smectic phase such as $S_C$, $S_F$, $S_G$, $S_H$, or $S_I$ phase, or a composition comprising a plurality of such compounds as a base material, and at least one ferroelectric liquid crystal compound or at least one optically active compound which per se is not a liquid crystal being mixed with the base material so that the resulting composition exhibits a ferroelectric liquid crystal phase.

As the base material in the composition (b) above, compounds or compositions exhibiting the non-chiral, tilted smectic phase are used as described above. In practical use, liquid crystals or liquid crystal compositions exhibiting the non-chiral, tilted smectic phase over a wide temperature range from lower temperature to higher than room temperature are desirable. Thus, of compounds exhibiting such non-chiral, tilted smectic phases, those exhibiting an Sc phase are widely employed as the base material, because the Sc phase appears in the highest temperature range among the phases wherein the ferroelectric phase is induced.

As such Sc phase liquid crystals, those such as phenylbenzoate-, Schiff base-, biphenyl-, phenylpyridine-, and phenylpyrimidine-based liquid crystals are used.

As optically active compounds to be added to the above base material to thereby induce ferroelectric properties, a number of compounds have been reported.

However, an optically active compound capable of providing a ferroelectric liquid crystal composition sufficiently meeting the aforementioned requirements has not been obtained.

SUMMARY OF THE INVENTION

An object of the present invention is to provide novel α-hydroxyketone derivatives as optically active compounds.

Another object of the present invention is to provide novel α-hydroxyketone derivatives which are optically active compounds inducing ferroelectric properties, and thus are useful for preparation of ferroelectric liquid crystal compositions.

Another object of the present invention is to provide novel α-hydroxyketone derivatives which are optically active compounds inducing a helical structure in nematic liquid crystal compositions, and thus are useful for preparation of chiral nematic liquid crystal compositions.

Another object of the present invention is to provide liquid crystal compositions containing the above α-hydroxyketone derivatives.

Another object of the present invention is to provide chiral smectic liquid crystal compositions containing the above α-hydroxyketone derivatives as optically active compounds.

Another object of the present invention is to provide chiral nematic liquid crystal compositions containing the above α-hydroxyketone derivatives as optically active compounds.

Another object of the present invention is to provide liquid crystal devices using the above liquid crystal compositions.

Other objects and advantages of the present invention will become apparent from the following detailed description.

The present invention relates to α-hydroxyketone derivatives represented by the general formula (I):

wherein:

A and B may be the same or different, and are independently a radical represented by the general formula (II):

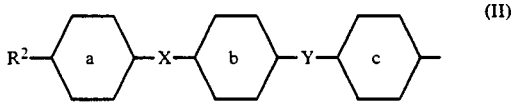

wherein R² is a saturated or unsaturated aliphatic hydrocarbon group having 1 to 16 carbon atoms, which may contain therein at least one ether bond, and may be substituted by at least one of a cyano group and a halogen atom,

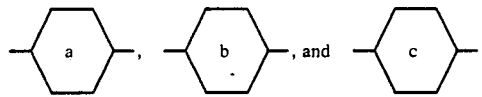

may be the same or different, and are independently a single bond,

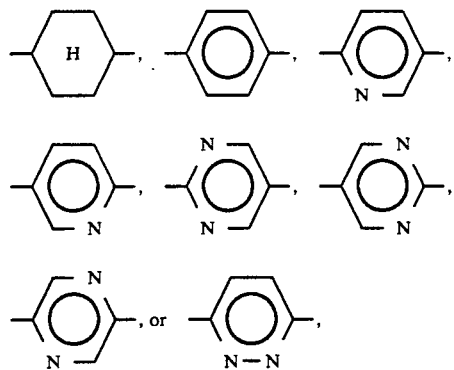

in which the radicals except for the single bond may be substituted by at least one of a cyano group and a halogen atom, and X and Y may be the same or different, and are independently a single bond, —CH₂CH₂—,

or —OCH₂—; or a saturated or unsaturated aliphatic hydrocarbon group having 1 to 16 carbon atoms, which may substituted by a radical represented by the above general formula (II);

R¹ is an alkyl group having 1 to 5 carbon atoms, a phenyl group, or a cyclohexyl group;

n is 0 or 1; and the asterisk * indicates an asymmetric carbon atom.

The present invention further relates to liquid crystal compositions containing at least one of the above α-hydroxyketone derivatives.

The present invention further relates to liquid crystal devices using the above liquid crystal compositions.

DETAILED DESCRIPTION OF THE INVENTION

In the above general formula (I), A and B may be the same or different, and are independently a radical represented by the above general formula (II), or a saturated or unsaturated aliphatic hydrocarbon group having 1 to 16 carbon atoms.

In the above general formula (II), R² is a saturated or unsaturated aliphatic hydrocarbon group having 1 to 16 carbon atoms, and may contain therein at least one ether bond (—O—). That is, this aliphatic hydrocarbon group may contain at least one double bond, or at least one triple bond, or at least one ether bond, or may contain at the same time two or more of at least one double bond, at least one triple bond, and at least one ether bond. Moreover, the aliphatic hydrocarbon group may be substituted by a cyano group, or a halogen atom, or both a cyano group and a halogen atom.

Typical examples of the aliphatic hydrocarbon group are a propyl group, a butyl group, a pentyl group, a hexyl group, a heptyl group, an octyl group, a nonyl group, a decyl group, an allyl group, a pentenyl group, a hexenyl group, a heptenyl group, an octenyl group, a butynyl group, a pentynyl group, a hexynyl group, a heptynyl group, an octynyl group, a butoxy group, a pentyloxy group, a hexyloxy group, a heptyloxy group, an octyloxy group, a nonyloxy group, and an allyloxy group.

In the above general formula (II),

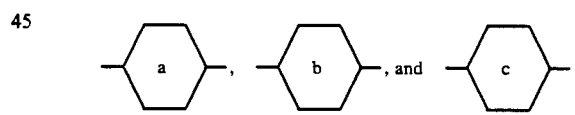

may be the same or different, and are independently a single bond,

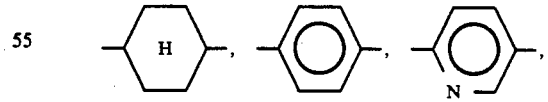

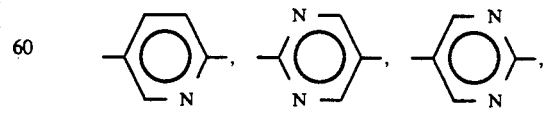

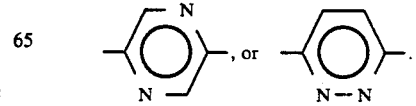

The above radicals except for the single bond may be substituted by a cyano group, or a halogen atom, or both a cyano group and a halogen atom.

In the above general formula (II), X and Y may be the same or different, and are independently a connecting group selected from a single bond, —CH₂CH₂—,

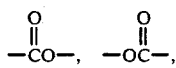

—CH₂O—, and —OCH₂—.

In the general formula (I), A and B may be independently a saturated or unsaturated aliphatic hydrocarbon group having 1 to 16 carbon atoms. This aliphatic hydrocarbon group may be substituted by at least one radical represented by the above general formula (II). That is, the aliphatic hydrocarbon group may contain at least one double bond, or at least one triple bond, or both at least one double bond and at least one triple bond, or may be substituted by a radical represented by the general formula (II) while containing or not containing at least one double bond, or at least one triple bond, or both at least one double bond and at least triple bond.

As typical examples of the aliphatic hydrocarbon group, the groups listed for the aliphatic hydrocarbon group represented by $R^2$ in the general formula (II) can be given.

Suitable examples of A in the general formula (I) include the groups represented by the following general formulas:

R'—,

R"—CH=CH—,

R"'—CH=CH—CH₂—,

R"—C≡C—,

R"'—C≡C—CH₂—,

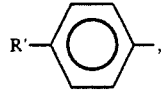

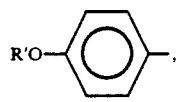

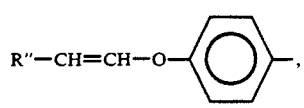

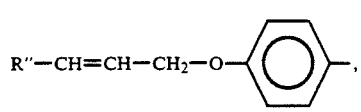

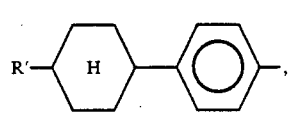

-continued

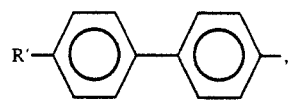

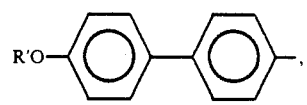

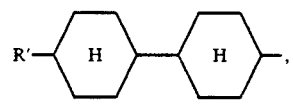

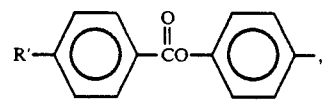

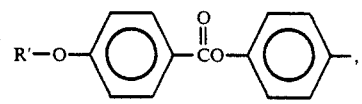

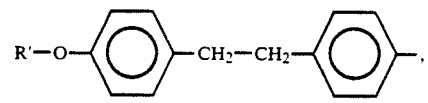

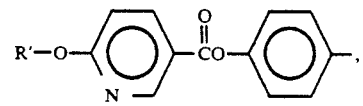

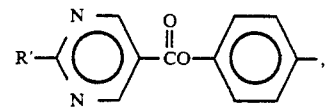

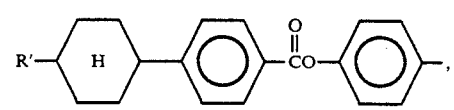

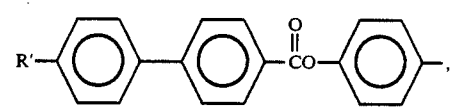

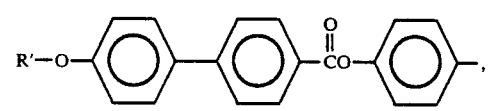

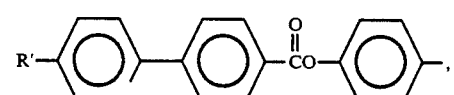

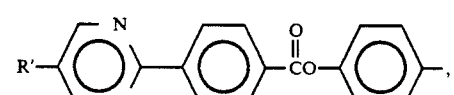

-continued

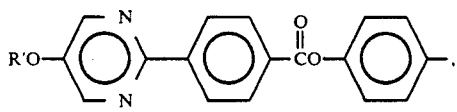

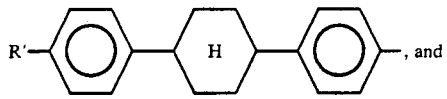

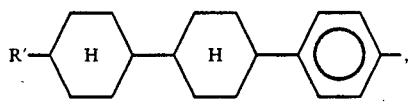

wherein R' is an alkyl group having 1 to 16 carbon atoms, and R'' is a hydrogen atom, or an alkyl group having 1 to 16 carbon atoms.

Suitable examples of B in the general formula (I) include the groups represented by the following general formulas:

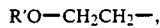

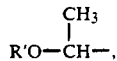

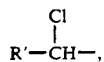

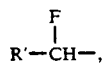

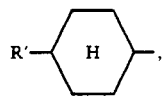

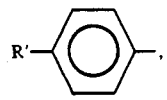

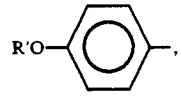

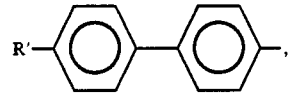

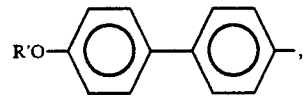

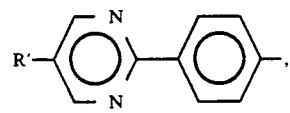

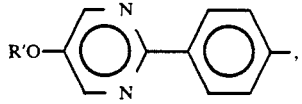

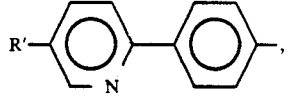

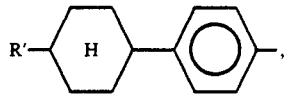

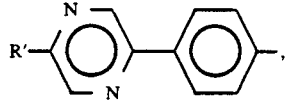

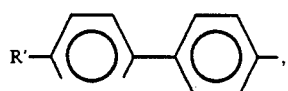

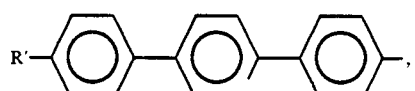

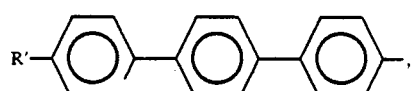

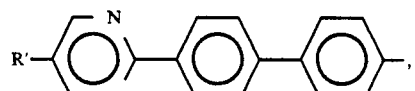

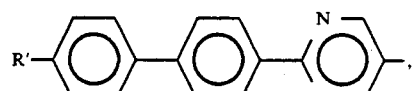

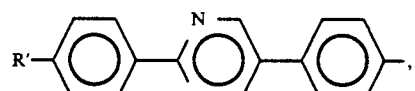

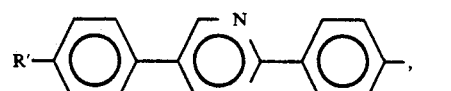

wherein R' is the same as defined above.

Of the groups represented by the above general formulas as listed above as suitable examples of A and B, groups of the above general formulas in which is an alkyl group or alkoxy group having 3 to 10 carbon atoms, such as a propyl group, a butyl group, a pentyl group, a hexyl group, a heptyl group, an octyl group, a nonyl group, a decyl group, a propoxy group, a butoxy group, a pentyloxy group, a hexyloxy group, a heptyloxy group, an octyloxy group, a nonyloxy group, or a decyloxy group are particularly preferred.

$R^1$ in the general formula (I) is an alkyl group having 1 to 5 carbon atoms, such as a methyl group, an ethyl group, a n-propyl group, an isopropyl group, a n-butyl group, an isobutyl group, a sec-butyl group, a tert-butyl group, or a pentyl group; a phenyl group; or a cyclohexyl group. Of these groups, a methyl group, an isopropyl group, and a phenyl group are particularly preferred.

Preferred examples of the compounds represented by the general formula (I) include the compounds represented by the following general formulas:

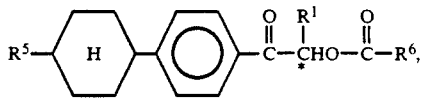

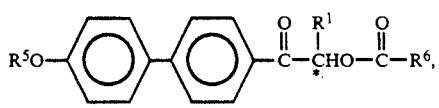

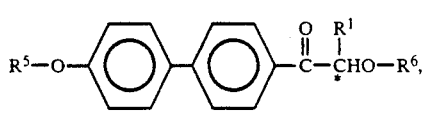

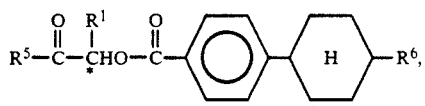

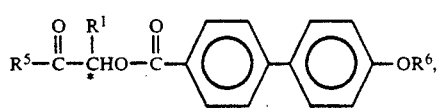

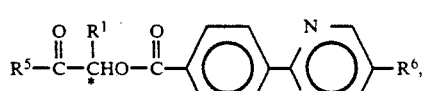

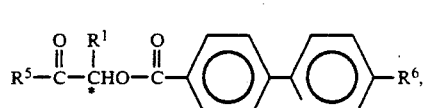

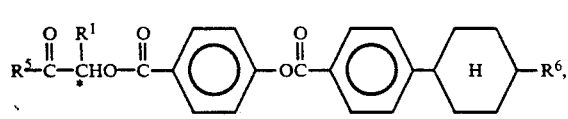

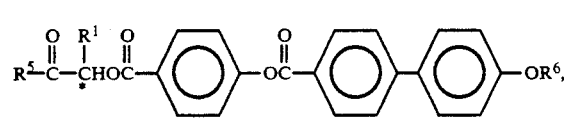

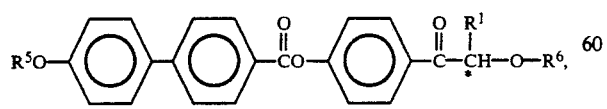

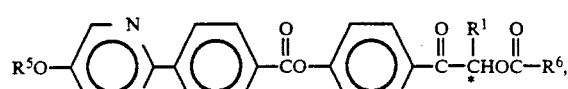

-continued

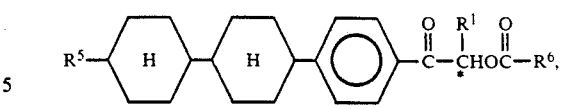

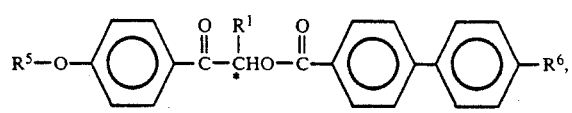

and

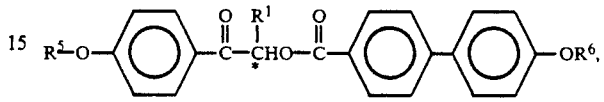

wherein $R^1$ is the same as defined above; $R^5$ is an alkyl group having 1 to 15 carbon atoms, an alkenyl group having 1 to 15 carbon atoms, or an alkynyl group having 1 to 15 carbon atoms; and $R^6$ is an alkyl group having 1 to 15 carbon atoms.

A typical method of preparation of the α-hydroxyketone derivatives of the general formula (I) is described below, although the present invention is not limited thereto.

(A) n=0 in the general formula (I)

In this case, the general formula (I) can be rewritten as the following general formula (I-a):

 (I-a)

wherein A, B, and $R^1$ are the same as defined above.

Compounds of the above general formula (I-a) can be prepared according to the process shown below.

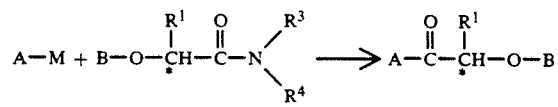

More specifically, a compound of the general formula (I-a) can be prepared by reacting an organometallic compound, e.g., organic lithium or a Grignard reagent, as represented by the general formula (III):

 (III)

wherein A is the same as defined above, and M indicates a metal such as lithium (Li), or magnesium bromide (MgBr), with an α-hydroxycarboxylic acid dialkylamide compound represented by the general formula (IV):

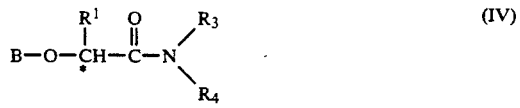 (IV)

wherein B and $R^1$ are the same as defined above, and $R^3$ and $R^4$ may be the same or different, and are independently a lower alkyl group such as a methyl group, an ethyl group, or a propyl group, usually in a solvent such as tetrahydrofuran or diethyl ether.

Reaction conditions are not critical, and the reaction can be carried out under conditions commonly employed in reactions of this type.

(B) n=1 in the general formula (I)

In this case, the general formula (I) can be rewritten as the following general formula (I-b):

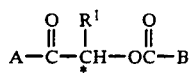   (I-b)

$$A-\overset{O}{\overset{\|}{C}}-\overset{R^1}{\underset{*}{\overset{|}{C}H}}-O\overset{O}{\overset{\|}{C}}-B$$

wherein A, B, and $R^1$ are the same as defined above.

Compounds of the above general formula (I-b) can be prepared according to the following reaction process:

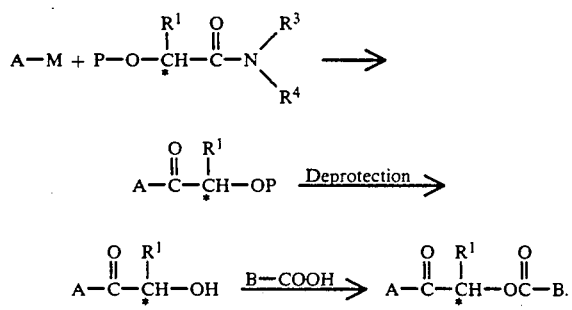

More specifically, a compound of the general formula (I-b) can be prepared by: reacting an organometallic compound represented by the above general formula (III):

   (III)

and an α-hydroxycarboxylic acid dialkylamide compound represented by the general formula (V):

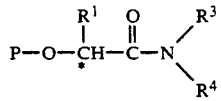   (V)

wherein $R^1$, $R^3$ and $R^4$ are the same as defined above, and P indicates a protective group such as a tetrapyranyl group or a 1-ethoxyethyl group to thereby obtain a ketone compound represented by the general formula (VI):

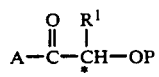   (VI)

wherein A, $R^1$, and P are the same as defined above;

removing the protective group from the ketone compound of the general formula (VI) to thereby obtain a hydroxyketone compound represented by the general formula (VII):

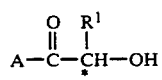   (VII)

wherein A and $R^1$ are the same as defined above; and reacting the hydroxyketone compound of the general formula (VII) as obtained above, with carboxylic acid represented by the general formula (VIII):

   (VIII)

wherein B is the same as defined above to thereby obtain the desired compound of the general formula (I-b).

An α-hydroxycarboxylic acid dialkylamide compound of the general formula (IV) to be used as a starting material in the above case (A) wherein n=0 can be prepared by reacting α-hydroxycarboxylic acid ester represented by the general formula (IX):

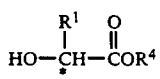   (IX)

wherein $R^1$ and $R^4$ are the same as defined above, with a compound represented by the general formula (X):

   (X)

wherein B is the same as defined above, and Hal indicates a leaving group such as a halogen atom, (e.g., bromine or iodine), or p-toluenesulfonyloxy, in the presence of an alkali such as silver oxide to thereby obtain an ether compound represented by the general formula (XI):

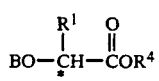   (XI)

wherein $R^1$ and $R^4$ are the same as defined above, and then reacting the ether compound of the general formula (XI) as obtained above, with dialkylamine represented by the general formula (XII):

   (XII)

wherein $R^3$ and $R^4$ are the same as defined above.

An α-hydroxycarboxylic acid dialkylamide compound of the general formula (V) to be used as a starting material in the above case (B) wherein n=1 can be prepared by reacting α-hydroxycarboxylic acid ester of the above general formula (IX) with dialkylamine of the above general formula (XII) to thereby obtain a compound represented by the general formula (XIII):

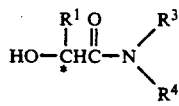   (XIII)

wherein $R^1$, $R^2$, and $R^3$ are the same as defined above, and then introducing thereinto a hydroxy group-protective group such as 1-ethoxyethyl or tetrahydropyranyl by the use of a protective agent such as ethylvinyl ether or dihydropyran.

Typical examples of the α-hydroxycarboxylic acid ester of the general formula (IX) are shown below.

(1) Alkyl lactate (this "alkyl" corresponds to the alkyl group of $R^4$; this is the same in the following compounds.)
(2) Alkyl α-hydroxybutanoate
(3) Alkyl α-hydroxy-β-methylbutanoate
(4) Alkyl α-hydroxypentanoate
(5) Alkyl α-hydroxy-γ-methylpentanoate
(6) Alkyl α-hydroxy-β-methylpentanoate
(7) Alkyl α-hydroxyhexanoate
(8) Alkyl α-hydroxypentanoate
(9) Alkyl mandelate
(10) Alkyl α-cyclohexyl-α-hydroxyacetate The above compounds (1), (9), and (10), and some of the compounds (2) to (8) are commercially available. The compounds (1) to (8) can be easily obtained by converting amino acids existing abundantly in nature into the corresponding diazonium salts, and then subjecting them to hydroxy replacing treatment. For example, the compound (3) is obtained from valine; the compound (5), from leucine; the compound (6), from isoleucine; and the compound (7), from norleucine. Moreover, the compounds (1) to (10) can be prepared by the use of a bio-catalyst such as microorganisms or enzymes.

When X or Y of the general formula (II) is

for example, and thus A of the general formula (I) is not stable against an organometallic reagent, and cannot constitute an organometallic compound represented by the general formula (III), i.e A-M, the compounds of the general formula (I) can be prepared, for example, by the methods as described below.

(A) n=0 in the general formula (I)

In this case, a compound of the general formula (I-a) can be prepared according to the process shown below.

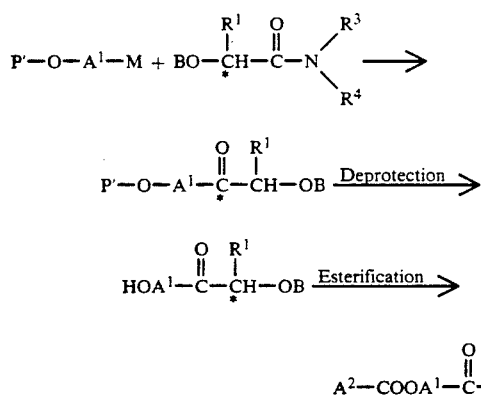

More specifically, a compound of the general formula (I-a) can be prepared by:

reacting an organometallic compound having the protected hydroxyl group as represented by the general formula (XIV):

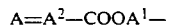 (XIV)

wherein M is the same as defined above, P' is a protective group, such as a benzyl group, a methoxymethyl group, or a methoxyethoxymethyl group, and $A^1$ and $A^2$ are such groups as to be represented by:

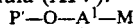

and a compound of the general formula (IV) to thereby obtain a compound with the hydroxyl group protected as represented by the general formula (XV):

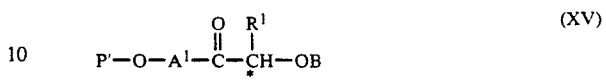 (XV)

wherein $R^1$, P' and B are the same as defined above; removing therefrom the protective group to thereby obtain a compound of the general formula (XVI):

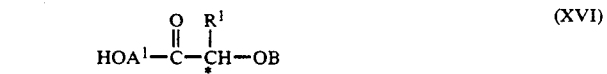 (XVI)

wherein $R^1$, $A^1$ and B are the same as defined above; and esterifying the compound of the general formula (XVI).

The aforementioned formula $A=A^2-COOA^1-$ corresponds to A of the general formula (II), for example, wherein

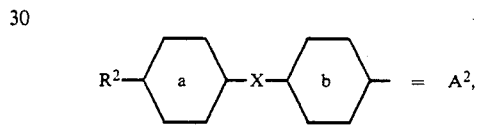

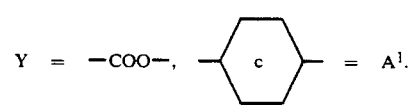

(B) n=1 in the general formula (I)

In this case, compounds of the general formula (I-b) can be prepared according to the process shown below.

P'—O—A$^1$—M +

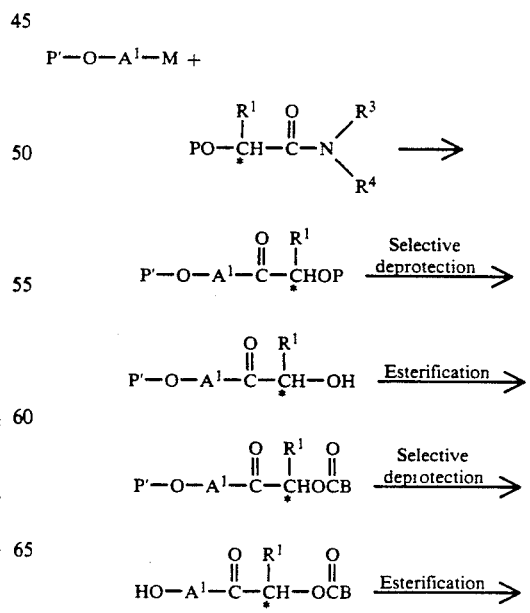

-continued

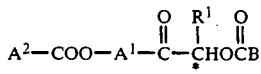

More specifically, a compound of the general formula (I-b) can be prepared by:

reacting an organometallic compound having a protected hydroxyl group as represented by the general formula (XIV), with a compound of the general formula (V) to thereby obtain a compound having protected hydroxyl groups at both ends thereof as represented by the general formula (XVII):

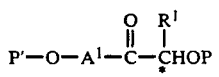 (XVII)

wherein $R^1$, $A^1$, P and P' are the same as defined above;

subjecting the compound of the general formula (XVII) to treatment to selectively remove the protective groups (P) to thereby obtain a compound of the general formula (XVIII):

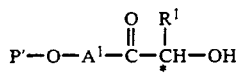 (XVIII)

wherein $R^1$, P' and $A^1$ are the same as defined above;

esterifying the compound of the general formula (XVIII) to thereby obtain a compound of the general formula (XIX):

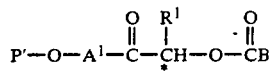 (XIX)

wherein $R^1$, P', $A^1$ and B are the same as defined above;

subjecting the compound of the general formula (XIX) to treatment to selectively remove the protective group (P') to thereby obtain a compound of the general formula (XX):

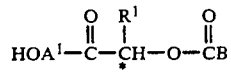 (XX)

wherein $R^1$, $A^1$ and B are the same as defined above; and finally esterifying the compound of the general formula (XX).

One of the features of the α-hydroxyketone derivatives of the general formula (I) is that they can induce high ferroelectric properties. More specifically, the α-hydroxyketone derivatives of the present invention, when added to a non-chiral, tilted smectic liquid crystal compound or compounds as a base material of a ferroelectric liquid crystal composition, induce ferroelectric properties, thereby providing a chiral smectic liquid crystal composition having a large spontaneous polarization value. This chiral smectic liquid crystal composition has a very high response speed because of the large spontaneous polarization value thereof, and thus is suitable as a material for use in quick response type liquid crystal devices such as animation displays.

The above-mentioned base material for a ferroelectric liquid crystal composition includes compounds having non-chiral tilted smectic phases such as an Sc phase. For practical use, liquid crystal compounds or liquid crystal compositions exhibiting the tilted smectic phase over a wide temperature range from a lower temperature to more than room temperature are preferred. Of these compounds, those having the Sc phase are particularly suitable because the Sc phase appears in the highest temperature range.

The above non-chiral, tilted smectic liquid crystal compounds to be used in the present invention are not critical; conventionally known compounds can be used. Typical examples of such compounds include the compounds represented by the following general formulas:

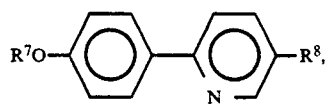
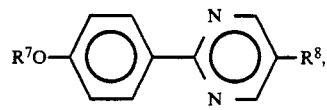
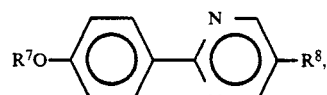
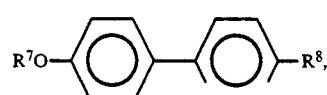
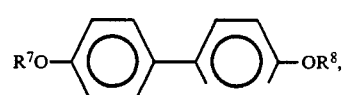
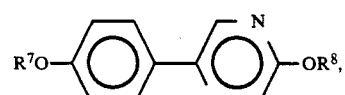
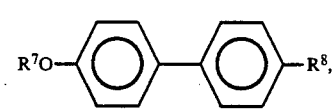
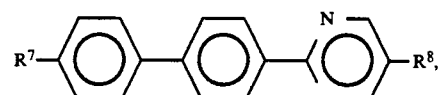
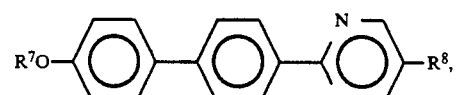
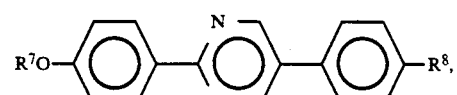

-continued

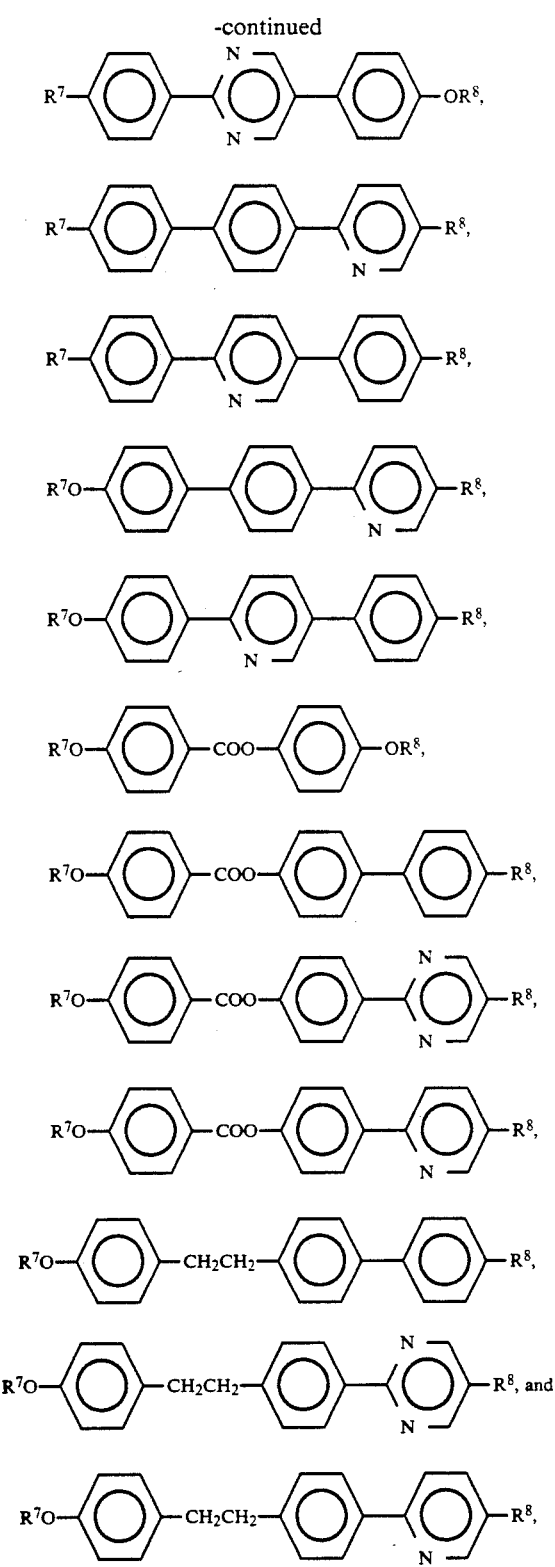

wherein R⁷ and R⁸ may be the same or different, and are independently an alkyl group having 1 to 20 carbon atoms, or an alkenyl group having 1 to 20 carbon atoms.

In chiral smectic liquid crystal compositions as ferroelectric liquid crystal compositions, as prepared by adding the α-hydroxyketone derivatives of the general formula (I) to non-chiral, smectic liquid crystal compounds as described above, the amount of the α-hydroxyketone derivatives used is 1 to 40% by weight, preferably 1 to 20% by weight based on the total weight of the composition. If the amount of the α-hydroxyketone derivative used is less than 1% by weight, satisfactorily high ferroelectric properties are not induced. On the other hand, if it is more than 40% by weight, the temperature range exhibiting the ferroelectric liquid crystal phase is narrowed.

In these chiral smectic liquid crystal compositions, to obtain negative dielectric anisotropy, compounds having structural units as shown below can be added.

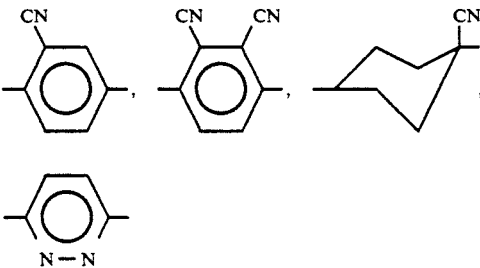

Another feature of the α-hydroxyketone derivatives of the general formula (I) is that they can induce a twist structure. More specifically, the α-hydroxyketone derivatives of the present invention, when added to nematic liquid crystal compounds, provide nematic liquid crystal compositions having a twisted structure, i.e., chiral nematic liquid crystal compositions.

The nematic liquid crystal compounds are not critical; conventionally known compounds or compositions can be used.

In these chiral nematic liquid crystal compositions, the amount of the α-hydroxyketone derivatives used is 0.01 to 5% by weight, preferably 0.1 to 3% by weight based on the total weight of the composition.

Main advantages of the present invention are shown below.

(1) The α-hydroxyketone derivatives of the present invention can induce high spontaneous polarization because they contain a carbonyl group having a large dipole moment. More specifically, the α-hydroxyketone derivatives of the present invention, when added to non-chiral smectic liquid crystal compound as the base material for ferroelectric liquid crystal compositions, provide chiral smectic liquid crystal compositions having a markedly high spontaneous polarization value.

(2) Chiral smectic liquid crystal compositions containing the α-hydroxyketone derivatives of the present invention have a greatly shortened response time because of the high spontaneous polarization thereof, and thus are very useful as quick response type liquid crystal device materials.

(3) The α-hydroxyketone derivatives of the present invention, when added to nematic liquid crystal compounds, can induce a twisted structure. More specifically, the α-hydroxyketone derivatives of the present invention, when added to nematic liquid crystal compounds, provide nematic liquid crystal compositions having the twist structure, i.e., chiral nematic liquid crystal compositions.

(4) Since chiral nematic liquid crystal compositions very seldom produce so-called reverse domain in TN mode display devices, the α-hydroxyketone derivatives of the present invention can be used to prevent the formation of reverse domain.

(5) The α-hydroxyketone derivatives of the present invention can be effectively used to impart a great twisting force necessary for super twisted nematic (STN) mode liquid crystal display devices which are now being generally employed as liquid crystal display devices, because they induce a very short chiral nematic pitch.

The present invention is described in greater detail with reference to the following examples, although it is not intended to be limited thereto. All percents (%) are by weight. Phase transition temperatures are in degrees centigrade.

EXAMPLE 1

In this example, (S) 1-methyl-2-keto-hexyl 4'-octyloxybiphenyl-4-ylcarboxylate (compound of the general formula (I) wherein:

A = —C$_4$H$_9$;

B = 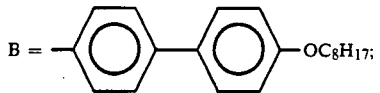—OC$_8$H$_{17}$;

R$^1$ = —CH$_3$; and
n = 1)

was prepared according to the process described below.

(1) Preparation of (S) N,N-dimethyllactamide 150 g (1.27 mol) of (S) ethyl lactate, and 100 g (2.22 mol) of anhydrous dimethylamine were placed in a pressure reactor, and reacted by heating at 80° C. for 30 hours. At the end of the reaction, the reaction mixture was distilled under reduced pressure to obtain 130 g of (S) N,N-dimethyllactamide (b.p., 65°–66° C./1.5 mmHg).

$\alpha_D^{25}$ −0.22 (neat)

(2) Preparation of (S) 1-ethoxyethyl-N,N-dimethyllactamide

A mixture of 130 g of (S) N,N-dimethyllactamide obtained in (1) above, 126 g of ethyl vinyl ether, and 500 ml of methylene chloride was cooled to 0° C., and a solution of 3 g of pyridinium p-toluenesulfonate (hereinafter abbreviated to "PPTS") in 50 ml of methylene chloride was dropped thereto. The resulting mixture was stirred at 0° C. for one hour, and then at room temperature for two hours, and, thereafter, was allowed to stand overnight.

The reactor was again cooled to about 0° C., and 1.2 g of solid sodium hydrogencarbonate was added thereto. The resulting mixture was stirred at about 0° C. for one hour, and then at room temperature for one hour. The methylene chloride was distilled away under reduced pressure. The remainder was subjected to column chromatographic purification by passing through a column packed with 100 g of silica gel, using a mixed solvent (1:3) of acetone and heptane as an eluting liquid.

The elutant thus obtained was concentrated, and then distilled under reduced pressure to obtain 201.8 g of (S) 1-ethoxyethyl-N,N-dimethyllactamide (b.p., 93–98° C./5 mmHg).

$\alpha_D^{26}$ −56.1 (neat)

(3) Preparation of (S) 2-hydroxy-3-heptanone

A solution of 40 g of (S) 1-ethoxyethyl-N,N-dimethyllactamide obtained in (2) above, dissolved in 400 ml of tetrahydrofuran (hereinafter abbreviated to "THF") was cooled to 0° C., and a solution of magnesium butylbromide prepared from 30 g of butyl bromide and 5.6 g of metallic magnesium, dissolved in 300 ml of THF was dropped thereto over two hours. The resulting mixture was stirred at 5°–10° C. for 3 hours, and then an aqueous solution containing 36 g of ammonium chloride was dropped thereto to complete the reaction.

The reaction mixture was extracted twice with 200 ml of heptane. The organic layer thus obtained was washed with water, dried, and then concentrated. The resulting concentrate was distilled under reduced pressure to obtain 26 g of (S) 2-(1-ethoxyethoxy)-3-heptanone (b.p., 68°–72° C./4 mmHg).

To this compound, 200 ml of ethanol and 1 g of PPTS were added, and the resulting mixture was stirred at room temperature for three hours. After the ethanol was distilled away, the remainder was distilled under reduced pressure to obtain 12 g of (S) 2-hydroxy-3-heptanone (b.p., 53°–55° C./3 mmHg).

$\alpha_D^{24}$ +34.1 (neat)

(4) Preparation of (S) 1-methyl-2-keto-hexyl 4'-octyloxy-biphenyl-4-ylcarboxylate 0.5 g of (S) 2-hydroxy-3-heptanone obtained in (3) above, 1.0 g of 4'-octyloxybiphenyl-4-ylcarboxylic acid chloride, and 30 ml of pyridine were reacted with stirring at 60° C. for 3 hours. After the completion of the reaction, 50 ml of toluene was added. The organic layer thus obtained was washed with an acid, an alkali, and then water, dried, and then concentrated. The remainder was subjected to column chromatographic purification by passing through a column packed with activated alumina using toluene as an eluting liquid, and then recrystallized from ethanol to obtain 0.6 g of (S) 1-methyl-2-keto-hexyl 4'-octyloxybiphenyl-4-ylcarboxylate (m.p., 90.2° C.).

In the same manner as above, the following compounds can be prepared.

1-Methyl-2-keto-pentyl 4'-hexylbiphenyl-4-yl-carboxylate
1-Methyl-2-keto-hexyl 4'-hexylbiphenyl-4-yl-carboxylate
1-Methyl-2-keto-heptyl 4'-hexylbiphenyl-4-yl-carboxylate
1-methyl-2-keto-octyl 4'-hexylbiphenyl-4-yl-carboxylate
1-Methyl-2-keto-pentyl 4'-heptylbiphenyl-4-yl-carboxylate
1-Methyl-2-keto-hexyl 4'-heptylbiphenyl-4-yl-carboxylate
1-Methyl-2-keto-heptyl 4'-heptylbiphenyl-4-yl-carboxylate
1-Methyl-2-keto-octyl 4'-heptylbiphenyl-4-yl-carboxylate
1-Methyl-2-keto-hexyl 4'-octylbiphenyl-4-yl-carboxylate
1-Methyl-2-keto-heptyl 4'-octylbiphenyl-4-yl-carboxylate
1-Methyl-2-keto-octyl 4'-octylbiphenyl-4-yl-carboxylate
1-Methyl-2-keto-pentyl 4'-hexylbiphenyl-4-yl-carboxylate
1-Methyl-2-keto-hexyl 4'-hexyloxybiphenyl-4-yl-carboxylate
1-Methyl-2-keto-heptyl 4'-hexyloxybiphenyl-4-yl-carboxylate
1-Methyl-2-keto-octyl 4'-hexyloxybiphenyl-4-yl-carboxylate 1-Methyl-2-keto-pentyl 4'-heptyloxybiphenyl-4-yl-carboxylate
1-Methyl-2-keto-hexyl 4'-heptyloxybiphenyl-4-yl-carboxylate
1-Methyl-2-keto-heptyl 4'-heptyloxybiphenyl-4-yl-carboxylate
1-Methyl-2-keto-octyl 4'-heptyloxybiphenyl-4-yl-carboxylate
1-Methyl-2-keto-pentyl 4'-hexyloxybiphenyl-4-yl-carboxylate
1-Methyl-2-keto-heptyl 4'-octyloxybiphenyl-4-yl-carboxylate
1-Methyl-2-keto-octyl 4'-octyloxybiphenyl-4-yl-carboxylate
1-Methyl-2-keto-pentyl 4-(5-hexylpyridin-2-yl)-benzoate
1-Methyl-2-keto-hexyl 4-(5-hexylpyridin-2-yl)-benzoate
1-Methyl-2-keto-heptyl 4-(5-hexylpyridin-2-yl)-benzoate
1-Methyl-2-keto-octyl 4-(5-hexylpyridin-2-yl)-benzoate
1-Methyl-2-keto-pentyl 4-(5-heptylpyridin-2-yl)-benzoate
1-Methyl-2-keto-hexyl 4-(5-heptylpyridin-2-yl)-benzoate
1-Methyl-2-keto-heptyl 4-(5-heptylpyridin-2-yl)-benzoate
1-Methyl-2-keto-octyl 4-(5-heptylpyridin-2-yl)-benzoate
1-Methyl-2-keto-pentyl 4-(5-octylpyridin-2-yl)-benzoate
1-Methyl-2-keto-hexyl 4-(5-octylpyridin-2-yl)-benzoate
1-Methyl-2-keto-heptyl 4-(5-octylpyridin-2-yl)-benzoate
1-Methyl-2-keto-octyl 4-(5-octylpyridin-2-yl)-benzoate
1-Methyl-2-keto-pentyl 4-(5-hexylpyrimidin-2-yl)-benzoate
1-Methyl-2-keto-hexyl 4-(5-hexylpyrimidin-2-yl)-benzoate
1-Methyl-2-keto-heptyl 4-(5-hexylpyrimidin-2-yl)-benzoate
1-Methyl-2-keto-octyl 4-(5-hexylpyrimidin-2-yl)-benzoate
1-Methyl-2-keto-pentyl 4-(5-heptylpyrimidin-2yl)-benzoate
1-Methyl-2-keto-hexyl 4-(5-heptylpyrimidin-2-yl)-benzoate
1-Methyl-2-keto-heptyl 4-(5-heptylpyrimidin-2yl)-benzoate
1-Methyl-2-keto-octyl 4-(5-heptylpyrimidin-2-yl)-benzoate
1-Methyl-2-keto-pentyl 4-(5-octylpyrimidin-2-yl)-benzoate
1-Methyl-2-keto-hexyl 4-(5-octylpyrimidin-2-yl)-benzoate
1-Methyl-2-keto-heptyl 4-(5-octylpyrimidin-2-yl)-benzoate
1-Methyl-2-keto-octyl 4-(5-octylpyrimidin-2-yl)-benzoate
1-Methyl-2-keto-hexyl 4-(4-hexyloxybenzoyloxy)-benzoate
1-Methyl-2-keto-heptyl 4-(4-hexyloxybenzoyloxy)-benzoate
1-Methyl-2-keto-octyl 4-(4-hexyloxybenzoyloxy)-benzoate
1-Methyl-2-keto-hexyl 4-(4-heptyloxybenzoyloxy)-benzoate
1-Methyl-2-keto-heptyl 4-(4-heptyloxybenzoyloxy)-benzoate
1-Methyl-2-keto-octyl 4-(4-heptyloxybenzoyloxy)-benzoate
1-Methyl-2-keto-hexyl 4-(4-octyloxybenzoyloxy)-benzoate
1-Methyl-2-keto-heptyl 4-(4-octyloxybenzoyloxy)-benzoate
1-Methyl-2-keto-octyl 4-(4-octyloxybenzoyloxy)-benzoate

EXAMPLE 2

(S) 1-Methyl-2-keto-3-octynyl 4-(5-octylpyrimidin-2-yl)benzoate (compound of the general formula (I) wherein:

$A = C_4H_9C\equiv C-$; 

$B =$ 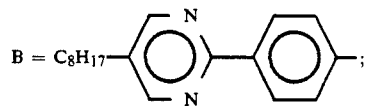;

$R^1 = CH_3-$; and $n = 1$)

was prepared by the process described below.

(1) Preparation of (S) 2-hydroxy-4-nonyn-3-one

A solution of 22 g of hexyne in 300 ml of THF was placed in a flask, and cooled to $-50°$ C. Then, 170 ml of a 1.55M n-hexane solution of n-butyllithium was dropped thereto. The resulting mixture was stirred at $-50°$ C. for 15 minutes, and then a solution of 50 g of (S) 1-ethoxyethyl-N,N-dimethyllactamide as obtained in Example 1 (2) in 150 ml of THF was dropped thereto. The resulting mixture was stirred at the same temperature as above for two hours, and then an aqueous solution of 28.3 g of ammonium chloride in 200 ml of water was dropped to terminate the reaction.

The reaction mixture was extracted twice with 200 ml of hexane. The organic layer thus obtained was washed with water, dried, and then concentrated. To the concentrate, 200 ml of p-dioxane, and 30 ml of concentrated hydrochloric acid were added, and the resulting mixture was stirred at $0°$ C. for two hours.

The mixture was extracted twice with 200 ml of chloroform. The organic layer thus obtained was washed with an alkali, and then with water, and concentrated.

The remainder thus obtained was distilled under reduced pressure to obtain 37 g of S-2-hydroxy-4-nonyne-3-one (b.p., $68°$ C./3.5 mmHg).

(2) Preparation of (S) 1-methyl-2-keto-3-octynyl 4-(5-octylpyrimidin-2-yl)benzoate A mixture of 1.0 g of (S) 2-hydroxy-4-nonyn-3-one obtained in (1) above, 2 g of 4-(5-octylpyrimidin-2-yl)benzoic acid chloride, 50 ml of pyridine, and 100 mg of 4-N,N-dimethylaminopyridine (hereinafter abbreviated to "DMAP") was reacted, and purified in the same manner as in Example 1 (4) to obtain the desired 1-methyl-2-keto-3-octynyl (S) 4-(5-octylpyrimidin-2-yl)-benzoate.

In the same manner as above, the following compounds can be prepared.

1-Methyl-2-keto-pentynyl 4-(trans-4-hexylcyclohexyl)-benzoate
1-Methyl-2-keto-hexynyl 4-(trans-4-hexylcyclohexyl)-benzoate
1-Methyl-2-keto-heptynyl 4-(trans-4-hexylcyclohexyl)-benzoate
1-Methyl-2-keto-octynyl 4-(trans-4-hexylcyclohexyl)-benzoate 1-Methyl-2-keto-pentynyl 4-(trans-4-heptylcyclohexyl)-benzoate
1-Methyl-2-keto-hexynyl 4-(trans-4-heptylcyclohexyl)-benzoate
1-Methyl-2-keto-heptynyl 4-(trans-4-heptylcyclohexyl)-benzoate
1-Methyl-2-keto-octynyl 4-(trans-4-heptylcyclohexyl)-benzoate
1-Methyl-2-keto-pentynyl 4-(trans-4-octylcyclohexyl)-benzoate
1-Methyl-2-keto-hexynyl 4-(trans-4-octylcyclohexyl)-benzoate
1-Methyl-2-keto-heptynyl 4-(trans-4-octylcyclohexyl)-benzoate
1-Methyl-2-keto-octynyl 4-(trans-4-octylcyclohexyl)-benzoate
1-Methyl-2-keto-pentynyl 4-(5-hexylpyrimidin-2-yl)benzoate
1-Methyl-2-keto-hexynyl 4-(5-hexylpyrimidin-2-yl)benzoate
1-Methyl-2-keto-heptynyl 4-(5-hexylpyrimidin-2-yl)benzoate
1-Methyl-2-keto-octynyl 4-(5-hexylpyrimidin-2-yl)benzoate
1-Methyl-2-keto-pentynyl 4-(5-heptylpyrimidin-2yl)-benzoate
1-Methyl-2-keto-hexynyl 4-(5-heptylpyrimidin-2yl)benzoate
1-Methyl-2-keto-heptynyl 4-(5-heptylpyrimidin-2-yl)benzoate
1-Methyl-2-keto-octynyl 4-(5-heptylpyrimidin-2-yl)benzoate
1-Methyl-2-keto-pentynyl 4-(5-octylpyrimidin-2-yl)benzoate
1-Methyl-2-keto-hexynyl 4-(5-octylpyrimidin-2-yl)benzoate
1-Methyl-2-keto-heptynyl 4-(5-octylpyrimidin-2-yl)benzoate
1-Methyl-2-keto-octynyl 4-(5-octylpyrimidin-2-yl)benzoate
1-Methyl-2-keto-hexynyl 4-(4'-hexyloxybiphenyl-4-yl-carbonyloxy)benzoate
1-Methyl-2-keto-heptynyl 4-(4'-hexyloxybiphenyl-4-yl-carbonyloxy)benzoate
1-Methyl-2-keto-octynyl 4-(4'-hexyloxybiphenyl-4-yl-carbonyloxy)benzoate
1-Methyl-2-keto-hexynyl 4-(4'-heptyloxybiphenyl-4-yl-carbonyloxy)benzoate
1-Methyl-2-keto-heptynyl 4-(4'-heptyloxybiphenyl-4-yl-carbonyloxy)benzoate
1-Methyl-2-keto-octynyl 4-(4'-heptyloxybiphenyl-4-yl-carbonyloxy)benzoate
1-Methyl-2-keto-hexynyl 4-(4'-octyloxybiphenyl-4-yl-carbonyloxy)benzoate
1-Methyl-2-keto-heptynyl 4-(4'-octyloxybiphenyl-4-yl-carbonyloxy)benzoate
1-Methyl-2-keto-octynyl 4-(4'-octyloxybiphenyl-4-yl-carbonyloxy)benzoate
1-Methyl-2-keto-hexynyl 4-(4'-hexyloxyphenylethyl)-benzoate
1-Methyl-2-keto-heptynyl 4-(4'-hexyloxyphenylethyl)-benzoate
1-Methyl-2-keto-octynyl 4-(4'-hexyloxyphenylethyl)-benzoate
1-Methyl-2-keto-hexynyl 4-(4'-heptyloxyphenylethyl)-benzoate
1-Methyl-2-keto-heptynyl 4-(4-heptyloxyphenylethyl)-benzoate
1-Methyl-2-keto-octynyl 4-(4'-heptyloxyphenylethyl)-benzoate
1-Methyl-2-keto-hexynyl 4-(4'-octyloxyphenylethyl)-benzoate
1-Methyl-2-keto-heptynyl 4-(4'-octyloxyphenylethyl)-benzoate
1-Methyl-2-keto-octynyl 4-(4'-octyloxyphenylethyl)-benzoate

EXAMPLE 3

(S) 4-(trans-4'-propylcyclohexyl)phenyl (1-pentanoyloxyethyl) ketone (compound of the general formula (I) wherein:

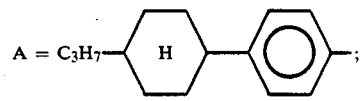
$A = C_3H_7-$ $B = C_4H_9-$;
$R^1 = CH_3-$; and
$n = 1$)

was prepared by the process described below.

(1) Preparation of (S) 4-(trans-4'-propylcyclohexyl)-phenyl (1-hydroxyethyl) ketone A solution of 4-(trans-4'-propylcyclohexyl)phenyl-magnesium bromide prepared from 10 g of 4-(trans-4'-propylcyclohexyl)bromobenzene and 1.0 g of metallic magnesium, dissolved in 100 ml of THF was dropped at 0° C. to a solution of 6.5 g of (S) 1-ethoxyethyl-N,N dimethyllactamide obtained in Example 1 (2) as dissolved in 200 ml of THF. The resulting mixture was stirred at 0–10° C. for three hours, and then an aqueous solution of 3.8 g of ammonium chloride was dropped thereto to terminate the reaction.

The resulting mixture was extracted twice with 100 ml of toluene. The organic layer thus obtained was washed with water, dried, and then concentrated. To the concentrate, 0.5 g of PPTS and 100 ml of ethanol were added, and the resulting mixture was stirred at room temperature for two hours. The ethanol was distilled away under reduced pressure. The remainder was purified by silica gel chromatography to obtain 3 g of the desired (S) 4-(trans-4'-propylcyclohexyl)phenyl (1-hydroxyethyl) ketone.

(2) Preparation of (S) 4-(trans-4'-propylcyclohexyl)-phenyl (1-pentanoyloxyethyl) ketone A mixture of 800 mg of (S) 4-(trans-4'-propylcyclohexyl)phenyl (1-hydroxyethyl) ketone obtained in (1) above, 540 mg of pentanoyl chloride, 100 ml of pyridine, and 100 mg of DMAP was stirred while heating for three hours. The reaction mixture was extracted twice with 100 ml of toluene. The organic layer thus obtained was washed with an acid, an alkali, and then water, and thereafter concentrated. The remainder was subjected to column chromatographic purification by passing through a column packed with activated alumina to obtain 600 mg of (S) 4-(trans-4'-propylcyclohexyl)-phenyl (1-pentanoyloxyethyl) ketone. This compound was liquid at room temperature.

$\alpha_D^{24} -10.1$ (C 0.7, CHCl$_3$)

In the same manner as above, the following compounds can be prepared.
4-(Trans-4'-propylcyclohexyl)phenyl (1-butanoyloxyethyl) ketone
4-(Trans-4'-propylcyclohexyl)phenyl (1-pentanoyloxyethyl) ketone 4-(Trans-4'-propylcyclohexyl)phenyl (1-hexanoyloxyethyl) ketone
4-(Trans-4'-pentylcyclohexyl)phenyl (1-butanoyloxyethyl) ketone
4-(Trans-4'-pentylcyclohexyl)phenyl (1-pentanoyloxyethyl) ketone
4-(Trans-4'-pentylcyclohexyl)phenyl (1-hexanoyloxyethyl) ketone
4-(Trans-4'-heptylcyclohexyl)phenyl (1-butanoyloxyethyl) ketone
4-(Trans-4'-heptylcyclohexyl)phenyl (1-pentanoyloxyethyl) ketone
4-(Trans-4'-heptylcyclohexyl)phenyl (1-hexanoyloxyethyl) ketone
4-(Trans-4'-hexylbiphenyl-4-yl) (1-butanoyloxyethyl) ketone
(4'-Hexyl-biphenyl-4-yl) (1-pentanoyloxyethyl) ketone
(4'-Hexyl-biphenyl-4-yl) (1-hexanoyloxyethyl) ketone
(4'-Heptyl-biphenyl-4-yl) (1-butanoyloxyethyl) ketone
(4'-Heptyl-biphenyl-4-yl) (1-pentanoyloxyethyl) ketone
(4'-Heptyl-biphenyl-4-yl) (1-hexanoyloxyethyl) ketone
(4'-Octyl-biphenyl-4-yl) (1-butanoyloxyethyl) ketone
(4'-Octyl-biphenyl-4-yl) (1-pentanoyloxyethyl) ketone
(4'-Octyl-biphenyl-4-yl) (1-hexanoyloxyethyl) ketone
(4'-Hexyloxy-biphenyl-4-yl) (1-butanoyloxyethyl) ketone
(4'-Hexyloxy-biphenyl-4-yl) (1-pentanoyloxyethyl) ketone
(4'-Hexyloxy-biphenyl-4-yl) (1-hexanoyloxyethyl) ketone
(4'-Heptyloxy-biphenyl-4-yl) (1-butanoyloxyethyl) ketone
(4'-Heptyloxy-biphenyl-4-yl) (1-pentanoyloxyethyl) ketone
(4'-Heptyloxy-biphenyl-4-yl) (1-hexanoyloxyethyl) ketone
(4'-Octyloxy-biphenyl-4-yl) (1-butanoyloxyethyl) ketone
(4'-Octyloxy-biphenyl-4-yl) (1-pentanoyloxyethyl) ketone
(4'-Octyloxy-biphenyl-4-yl) (1-hexanoyloxyethyl) ketone

EXAMPLE 4

(S) 1-Methyl-2-(4'-allyloxyphenyl)-2-keto-ethyl 4'-heptyl-biphenyl-4-ylcarboxylate (compound of the general formula (I) wherein:

A = CH$_2$=CH—CH$_2$—O— 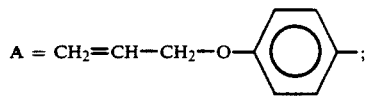 ;

B = C$_7$H$_{15}$— 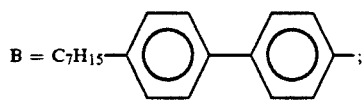 ;

R$^1$=CH$_3$—; and
n=1)
was prepared by the process described below.

(1) Preparation of 1-(4-allyloxyphenyl)-3-hydroxy-2-propane

A solution of 22 g of (S) 1-ethoxyethyl-N,N-dimethyllactamide obtained in Example 1 (2) in 150 ml of THF was cooled to 0° C., and a solution of 4-allyloxyphenylmagnesium bromide prepared from 25 g of 4-allyloxybromobenzene and 3 g of magnesium, in 200 ml of THF was added thereto over two hours. After the completion of addition, the resulting mixture was stirred at 0-5° C. for three hours, and then an aqueous solution containing 12.6 g of ammonium chloride was added thereto to terminate the reaction.

The resulting mixture was extracted twice with 100 ml of toluene. The organic layer thus obtained was washed with water, dried, concentrated, and then distilled under reduced pressure to obtain 15 g of a compound protected by an ethoxyethyl group (b.p., 160°-168° C./4 mmHg). To this compound, 0.5 g of PPTS and 100 ml of ethanol were added, and the resulting mixture was stirred at room temperature for two hours.

After addition of 200 ml of water, the resulting mixture was extracted with toluene. The organic layer thus obtained was washed with an alkali and then water, dried, and then concentrated. The remainder was distilled under reduced pressure to obtain 5.6 g of (S) 1-(4-allyloxyphenyl)-2-hydroxy-1-propanone (b.p., 152°-155° C./4.5 mmHg).

$\alpha_D{}^{24}$ −60.2 (C 1.89, CHCl$_3$)

(2) Preparation of (S) 1-methyl-2-(4'-allyloxyphenyl)-2-keto-ethyl 4'-heptylbiphenyl-4-ylcarboxylate A mixture of 1.8 g of 4'-heptylbiphenyl-4-ylcarboxylic acid chloride, 1.2 g of (S) 1-(4-allyloxy-phenyl)-2-hydroxy-1-propanone obtained in (1) above, 50 ml of pyridine, and 200 mg of DMAP was reacted, and purified in the same manner as in Example 1 (4) to obtain 1.2 g of the desired (S) 1-methyl-2-(4'-allyloxy-phenyl)-2-keto-ethyl 4'-heptylbiphenyl-4-ylcarboxylate. This compound exhibited the following phase transition:
Cr 80.7 S$_A$ 86.8 I.

In the same manner as above, the following compounds can be prepared.

1-Methyl-2-(4-butylphenyl)-2-keto-ethyl 4'-hexylbiphenyl-4-ylcarboxylate
1-Methyl-2-(4-butylphenyl)-2-keto-ethyl 4'-heptylbiphenyl-4-ylcarboxylate
1-Methyl-2-(4-butylphenyl)-2-keto-ethyl 4'-octylbiphenyl-4-ylcarboxylate
1-Methyl-2-(4-butylphenyl)-2-keto-ethyl 4'-hexyloxybiphenyl-4-ylcarboxylate
1-Methyl-2-(4-butylphenyl)-2-keto-ethyl 4'-hexyloxybiphenyl-4-ylcarboxylate
1-Methyl-2-(4-butylphenyl)-2-keto-ethyl 4'-octyl-hexylbiphenyl-4-ylcarboxylate
1-Methyl-2-(4-butylphenyl)-2-keto-ethyl 4-hexylbenzoate
1-Methyl-2-(4-butylphenyl)-2-keto-ethyl 4-heptylbenzoate
1-Methyl-2-(4-butylphenyl)-2-keto-ethyl 4-octylbenzoate
1-Methyl-2-(4-butylphenyl)-2-keto-ethyl 4-(5-hexylpyrimidin-2-yl)benzoate
1-Methyl-2(4-butylphenyl)-2-keto-ethyl 4(5-heptylpyrimidin-2-yl)benzoate
1-Methyl-2-(4-butylphenyl)-2-keto-ethyl 4-(5-octylpyrimidin-2-yl)benzoate
1-Methyl-2-(4-butylphenyl)-2-keto-ethyl 4-(5-hexylpyridin-2-yl)benzoate
1-Methyl-2-(4-butylphenyl)-2-keto-ethyl 4-(5-heptylpyridin-2-yl)benzoate
1-Methyl-2-(4-butylphenyl)-2-keto-ethyl 4-(5-octylpyridin-2-yl)benzoate
1-Methyl-2-(4-butylphenyl)-2-keto-ethyl 4'-hexylbiphenyl-4-ylcarboxylate 1-Methyl-2-(4-butylphenyl)-2-keto-ethyl 4'-heptylbiphenyl-4-ylcarboxylate
1-Methyl-2-(4-butylphenyl)-2-keto-ethyl 4'-octylbiphenyl-4-ylcarboxylate
1-Methyl-2-(4-butylphenyl)-2-keto-ethyl 4'-hexyloxybiphenyl-4-ylcarboxylate
1-Methyl-2-(4-butylphenyl)-2-keto-ethyl 4'-heptyloxybiphenyl-4-ylcarboxylate
1-Methyl-2-(4-butylphenyl)-2-keto-ethyl 4'-octyloxybiphenyl-4-ylcarboxylate
1-Methyl-2-(4-butylphenyl)-2-keto-ethyl 4-hexylbenzoate
1-Methyl-2-(4-butylphenyl)-2-keto-ethyl 4-heptylbenzoate
1-Methyl-2-(4-butylphenyl)-2-keto-ethyl 4-octylbenzoate
1-Methyl-2-(4-butylphenyl)-2-keto-ethyl 4-(5-hexylpyrimidin-2-yl)benzoate
1-Methyl-2-(4-butylphenyl)-2-keto-ethyl 4-(5-heptylpyrimidin-2-yl)benzoate
1-Methyl-2-(4-butylphenyl)-2-keto-ethyl 4-(5-octylpyrimidin-2-yl)benzoate
1-Methyl-2-(4-butylphenyl)-2-keto-ethyl 4-(5-hexylpyridin-2-yl)benzoate
1-Methyl-2-(4-butylphenyl)-2-keto-ethyl 4-(5-heptylpyridin-2-yl)benzoate
1-Methyl-2-(4-butylphenyl)-2-keto-ethyl 4-(5-octylpyridin-2-yl)benzoate
1-Methyl-2-(4-allyloxyphenyl)-2-keto-ethyl 4'-hexylbiphenyl-4-ylcarboxylate
1-Methyl-2-(4-allyloxyphenyl)-2-keto-ethyl 4'-octylbiphenyl-4-ylcarboxylate
1-Methyl-2-(4-allyloxyphenyl)-2-keto-ethyl 4'-hexyloxybiphenyl-4-ylcarboxylate
1-Methyl-2-(4-allyloxyphenyl)-2-keto-ethyl 4'-heptyloxybiphenyl-4-ylcarboxylate
1-Methyl-2-(4-allyloxyphenyl)-2-keto-ethyl 4'-octyloxybiphenyl-4-ylcarboxylate
1-Methyl-2-(4-allyloxyphenyl)-2-keto-ethyl 4-hexylbenzoate
1-Methyl-2-(4-allyloxyphenyl)-2-keto-ethyl 4-heptylbenzoate
1-Methyl-2-(4-allyloxyphenyl)-2-keto-ethyl 4-octylbenzoate
1-Methyl-2-(4-allyloxyphenyl)-2-keto-ethyl 4-hexyloxybenzoate
1-Methyl-2-(4-allyloxyphenyl)-2-keto-ethyl 4-heptyloxybenzoate
1-Methyl-2-(4-allyloxyphenyl)-2-keto-ethyl 4-octyloxybenzoate (m.p. 55.5° C.)
1-Methyl-2-(4-allyloxyphenyl)-2-keto-ethyl 4-(5-hexylpyrimidin-2-yl)benzoate
1-Methyl-2-(4-allyloxyphenyl)-2-keto-ethyl 4-(5-heptylpyrimidin-2-yl)benzoate
1-Methyl-2-(4-allyloxyphenyl)-2-keto-ethyl 4-(5-octylpyrimidin-2-yl)benzoate
1-Methyl-2-(4-allyloxyphenyl)-2-keto-ethyl 4-(5-hexylpyridin-2-yl)benzoate
1-Methyl-2-(4-allyloxyphenyl)-2-keto-ethyl 4-(5-heptylpyridin-2-yl)benzoate
1-Methyl-2-(4-allyloxyphenyl)-2-keto-ethyl 4-(5-octylpyridin-2-yl)benzoate
1-Methyl-2-(4-allyloxyphenyl)-2-keto-ethyl 4-hexylbenzoate
1-Methyl-2-(4-allyloxyphenyl)-2-keto-ethyl 4heptylbenzoate
1-Methyl-2-(4-allyloxyphenyl)-2-keto-ethyl 4-octylbenzoate
1-Methyl-2-(4-allyloxyphenyl)-2-keto-ethyl 4-(4pentylcyclohexyl)benzoate (Cr 86.6 $S_A$ 87.7 I)
1-Methyl-2-(4-allyloxyphenyl)-2-keto-ethyl 4-(4hexylcyclohexyl)benzoate
1-Methyl-2-(4-allyloxyphenyl)-2-keto-ethyl 4-(4-heptylcyclohexyl)benzoate
1-Methyl-2-(4-allyloxyphenyl)-2-keto-ethyl 4-(4octylcyclohexyl)benzoate
1-Methyl-2-(4-allyloxyphenyl)-2-keto-ethyl 4-(5-hexylpyrimidin-2-yl)benzoate
1-Methyl-2-(4-allyloxyphenyl)-2-keto-ethyl 4-(5-heptylpyrimidin-2-yl)benzoate
1-Methyl-2-(4-allyloxyphenyl)-2-keto-ethyl 4-(5-octylpyrimidin-2-yl)benzoate
1-Methyl-2-(4-allyloxyphenyl)-2-keto-ethyl 4-(5-hexylpyridin-2-yl)benzoate
1-Methyl-2-(4-allyloxyphenyl)-2-keto-ethyl 4-(5-heptylpyridin-2-yl)benzoate
1-Methyl-2-(4-allyloxyphenyl)-2-keto-ethyl 4-(5-octylpyridin-2-yl)benzoate

EXAMPLE 5

(S) 4-(2-Pentanoyloxy-1-keto-propyl)phenyl 4'-octyloxybiphenyl-4-ylcarboxylate (compound of the general formula (I) wherein:

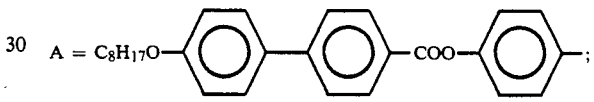

$B = C_4H_9-$;
$R^1 = CH_3-$; and
$n = 1$)
was prepared according to the process described below.

(1) Preparation of (S) 1-(4-methoxyethoxymethoxyphenyl)-2-hydroxy-1-propanone

A solution of 20 g of (S) 1-ethoxyethyl-N,N-dimethyllactamide obtained in Example 1 (2) in 200 ml of THF was cooled to 0° C, and a solution of 4-methoxyethoxymethoxyphenylmagnesium bromide prepared from 28 g of 4-methoxyethoxymethoxybromobenzene and 2.6 g of metallic magnesium, in 150 ml of THF was dropped thereto over one hour. The resulting mixture was stirred at 5° C. for two hours, and then an aqueous solution of 11.5 g of ammonium chloride was dropped thereto.

The resulting mixture was extracted twice with 100 ml of toluene. The organic layer thus obtained was washed with water, dried, and then concentrated. The remainder was distilled under reduced pressure to obtain 20.0 g of a compound protected by an ethoxyethyl group (b.p., 178–186° C./3 mmHg).

$a_D^{29}$ −58.5 (C 1.4, CHCl$_3$)

To this compound, 0.5 g of PPTS and 100 ml of ethanol were added, and the resulting mixture was stirred at room temperature. After addition of water, the mixture was extracted with toluene. The organic layer thus obtained was neutralized, washed with water, dried, and then concentrated to obtain the desired (S) 1-(4-methoxyethoxymethoxyphenyl)-2-hydroxy-1-propane.

$a_D^{25}$ −38.5 (neat)

(2) Preparation of (S) 4-(2-pentanoyloxy-1-ketopropyl)-phenol

A mixture of 4.0 g of (S) 1-(4-methoxyethoxymethoxyphenyl)-2-hydroxy-1-propanone, 3.0 g of pentanoyl chloride, 50 ml of pyridine, and 100 mg of DMAP was reacted, and purified in the same manner as in Example 1 (4) to obtain 5.5 g of (S) 1-(4-methoxyethoxymethoxyphenyl)-2-pentanoyloxypropanone. To this product, 50 ml of methylene chloride and 1.5 g of trifluoromethanesulfonic acid were added, and they were stirred at room temperature for three hours. The reaction mixture was washed with water and then with an alkali, dried, and then concentrated to obtain 2.0 g of (S) 4-(2-petanoyloxy-1-keto-propyl)phenol.

(3) Preparation of (S) 4-(2-pentanoyloxy-1-ketopropyl)-phenyl 4'-octyloxybiphenyl-4-ylcarboxylate A mixture of 500 mg of 4'-octyloxy-biphenyl-4-ylcarboxylic acid chloride, 400 mg of (S) 4-(2-pentanoyloxy-1-keto-propyl)phenol, 600 mg of N,N-dicyclohexylcarbodiimide, and 20 mg of DMAP was stirred at room temperature for three hours. A solid material precipitated was removed by filtration. The organic layer thus obtained was washed with an acid, an alkali, and with water, dried, and then concentrated.

The remainder was purified by passing through a column packed with activated alumina using toluene as an eluting liquid to obtain 300 mg of (S) 4-(2-pentanoyloxy-1-keto-propyl)phenyl 4'-octyloxy-biphenyl-4-yl-carboxylate. This compound exhibited the following phase transition:

Cr 74.9 ($S_4^*$ 10, $S_3^*$25) $S_C^*$101.0 $S_A$ 146.8 I.

In the same manner as above, the following compounds can be prepared.

4-(2-Butanoyloxy-1-keto-propyl)phenyl 4'-hexyloxybiphenyl-4-ylcarboxylate
4-(2-Pentanoyloxy-1-keto-propyl)phenyl 4'-hexyloxybiphenyl-4-ylcarboxylate
4-(2-Hexnoyloxy-1-keto-propyl)phenyl 4'-hexyloxybiphenyl-4-ylcarboxylate
4-(2-Butanoyloxy-1-keto-propyl)phenyl 4'-octyloxybiphenyl-4-ylcarboxylate
4-(2-Pentanoyloxy-1-keto-propyl)phenyl 4'-octyloxybiphenyl-4-ylcarboxylate
4-(2-Hexanoyloxy-1-keto-propyl)phenyl 4'-octyloxybiphenyl-4-ylcarboxylate
4-(2-Butanoyloxy-1-keto-propyl)phenyl 4'-heptylbiphenyl-4-ylcarboxylate
4-(2-Pentanoyloxy-1-keto-propyl)phenyl 4'-heptylbiphenyl-4-ylcarboxylate
4-(2-Hexanoyloxy-1-keto-propyl)phenyl 4'-heptylbiphenyl-4-ylcarboxylate
4-(2-Butanoyloxy-1-keto-propyl)phenyl 4-(5-hexylpyrimidin-2-yl)benzoate
4-(2-Heptanoyloxy-1-keto-propyl)phenyl 4-(5-hexylpyrimidin-2-yl)benzoate
4-(2-Hexanoyloxy-1-keto-propyl)phenyl 4-(5-hexylpyrimidin-2-yl)benzoate
4-(2-Butanoyloxy-1-keto-propyl)phenyl 4-(5-heptylpyrimidin-2-yl)benzoate
4-(2-Heptanoyloxy-1-keto-propyl)phenyl 4-(5-heptylpyrimidin-2-yl)benzoate
4-(2-Hexanoyloxy-1-keto-propyl)phenyl 4-(5-heptylpyrimidin-2-yl)benzoate
4-(2-Butanoyloxy-1-keto-propyl)phenyl 4-(5-octylpyrimidin-2-yl)benzoate
4-(2-Heptanoyloxy-1-keto-propyl)phenyl 4-(5-octylpyrimidin-2-yl)benzoate
4-(2-Hexanoyloxy-1-keto-propyl)phenyl 4-(5-octylpyrimidin-2-yl)benzoate
4-(2-Butanoyloxy-1-keto-propyl)phenyl 4-(5-hexylpyridin-2-yl)benzoate
4-(2-Heptanoyloxy-1-keto-propyl)phenyl 4-(5-hexylpyridin-2-yl)benzoate
4-(2-Hexanoyloxy-1-keto-propyl)phenyl 4-(5-hexylpyridin-2-yl)benzoate
4-(2-Butanoyloxy-1-keto-propyl)phenyl 4-(5-heptylpyridin-2-yl)benzoate
4-(2-Heptanoyloxy-1-keto-propyl)phenyl 4-(5-heptylpyridin-2-yl)benzoate
4-(2-Hexanoyloxy-1-keto-propyl)phenyl 4-(5-heptylpyridin-2-yl)benzoate
4-(2-Butanoyloxy-1-keto-propyl)phenyl 4-(5-octylpyridin-2-yl)benzoate
4-(2-heptanoyloxy-1-keto-propyl)phenyl 4-(5-octylpyridin-2-yl)benzoate
4-(2-Hexanoyloxy-1-keto-propyl)phenyl 4-(5-octylpyridin-2-yl)benzoate
4-(2-Butanoyloxy-1-keto-propyl)phenyl 4-hexylbenzoate
4-(2-Heptanoyloxy-1-keto-propyl)phenyl 4-hexylbenzoate
4-(2-Hexanoyloxy-1-keto-propyl)phenyl 4-hexylbenzoate
4-(2-Butanoyloxy-1-keto-propyl)phenyl 4-heptylbenzoate
4-(2-Heptanoyloxy-1-keto-propyl)phenyl 4-heptylbenzoate
4-(2-Hexanoyloxy-1-keto-propyl)phenyl 4-heptylbenzoate
4-(2-Butanoyloxy-1-keto-propyl)phenyl 4-octylbenzoate
4-(2-Heptanoyloxy-1-keto-propyl)phenyl 4-octylbenzoate
4-(2-Hexanoyloxy-1-keto-propyl)phenyl 4-octylbenzoate
4-(2-Butanoyloxy-1-keto-propyl)phenyl 4-hexyloxybenzoate
4-(2-Heptanoyloxy-1-keto-propyl)phenyl 4-hexyloxybenzoate
4-(2-Hexanoyloxy-1-keto-propyl)phenyl 4-hexyloxybenzoate
4-(2-Butanoyloxy-1-keto-propyl)phenyl 4-heptyloxybenzoate
4-(2-Heptanoyloxy-1-keto-propyl)phenyl 4-heptyloxybenzoate
4-(2-Hexanoyloxy-1-keto-propyl)phenyl 4-heptyloxybenzoate
4-(2-Butanoyloxy-1-keto-propyl)phenyl 4-octyloxybenzoate
4-(2-Heptanoyloxy-1-keto-propyl)phenyl 4-octyloxybenzoate
4-(2-Hexanoyloxy-1keto-propyl)phenyl 4-octyloxybenzoate

EXAMPLE 6

(R) 4-(trans-4'-propylcyclohexyl)phenyl (1-butoxyethyl) ketone (compound of the general formula (I) wherein:

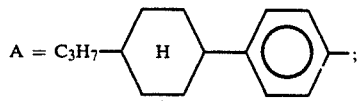

$B = C_4H_9-$;
$R^1 = CH_3-$; and
$n = 0$)

is prepared according to the process described below.

To (R) 2-butoxy-N,N-dimethylpropanamide prepared from (R) 2-butoxypropionic acid and dimethylamine, a solution of 4-(trans-4'-propylcyclohexyl)-phenylmagnesium bromide in THF is dropped. They are reacted and purified in the same manner as in Example 3 (1) to obtain (R) 4-trans-4'-propylcyclohexyl)phenyl (1-butoxyethyl) ketone.

In the same manner as above, the following compounds can be prepared.

4-(Trans-4'-propylcyclohexyl)phenyl (1-butoxyethyl) ketone
4-(Trans-4'-propylcyclohexyl)phenyl (1-pentyloxyethyl) ketone
4-(Trans-4'-propylcyclohexyl)phenyl (1-hexyloxyethyl) ketone
4-(Trans-4'-pentylcyclohexyl)phenyl (1-butoxyethyl) ketone
4-(Trans-4'-pentylcyclohexyl)phenyl (1-pentyloxyethyl) ketone
4-(Trans-4'-pentylcyclohexyl)phenyl (1-hexyloxyethyl) ketone
4-(Trans-4'-pentylcyclohexyl)phenyl (1-butoxyethyl) ketone
4-(Trans-4'-heptylcyclohexyl)phenyl (1-pentyloxyethyl) ketone
4-(Trans-4'-heptylcyclohexyl)phenyl (1-hexyloxyethyl) ketone
(4'-Hexyl-biphenyl-4-yl) (1-butoxyethyl) ketone
(4'-Hexyl-biphenyl-4-yl) (1-pentyloxyethyl) ketone
(4'-Hexyl-biphenyl-4-yl) (1-hexyloxyethyl) ketone
(4'-Heptyl-biphenyl-4-yl) (1-butoxyethyl) ketone
(4'-Heptyl-biphenyl-4-yl) (1-pentyloxyethyl) ketone
(4'-Heptyl-biphenyl-4-yl) (1-hexyloxyethyl) ketone
(4'-Octyl-biphenyl-4-yl) (1-butoxyethyl) ketone
(4'-Octyl-biphenyl-4-yl) (1-pentyloxyethyl) ketone
(4'-Octyl-biphenyl-4-yl) (1-hexyloxyethyl) ketone
(4'-Hexyloxy-biphenyl-4-yl) (1-butoxyethyl) ketone
(4'-Hexyloxy-biphenyl-4-yl) (1-pentyloxyethyl) ketone
(4'-Hexyloxy-biphenyl-4-yl) (1-hexyloxyethyl) ketone
(4'-Heptyloxy-biphenyl-4-yl) (1-butoxyethyl) ketone
(4'-Heptyloxy-biphenyl-4-yl) (1-pentyloxyethyl) ketone
(4'-Heptyloxy-biphenyl-4-yl) (1-hexyloxyethyl) ketone
(4'-Octyloxy-biphenyl-4-yl) (1-butoxyethyl) ketone
(4'-Octyloxy-biphenyl-4-yl) (1-pentyloxyethyl) ketone
(4'-Octyloxy-biphenyl-4-yl) (1-hexyloxyethyl) ketone

EXAMPLE 7

(S) 4-(2-pentanoyloxy-1-keto-propyl)phenyl 4'-octyloxybiphenyl-4-ylcarboxylate prepared in Example 5 was filled in a 10 μm thick cell equipped with transparent electrodes, which had been subjected to aligning treatment by coating with polyvinyl alcohol as an aligning agent followed by rubbing of the surface thereof, and measured for spontaneous polarization (Ps) and tilt angle. The results are shown in Table 1.

TABLE 1

| Temp. (°C.) | Ps (nc/cm$^2$) | Tilt Angle (°) |
|---|---|---|
| 95 | 33.8 | 17.3 |
| 90 | 46.9 | 21.4 |
| 85 | 59.6 | 23.7 |
| 80 | 69.4 | 25.0 |
| 70 | 90.0 | 27.0 |
| 30 | 187.6 | 30.0 |

It can be seen from the results of Table 1 that the compound of the present invention, when exhibits ferroelectric properties by itself, shows high spontaneous polarization, and thus is useful as a suitable material for use in quick response devices.

EXAMPLE 8

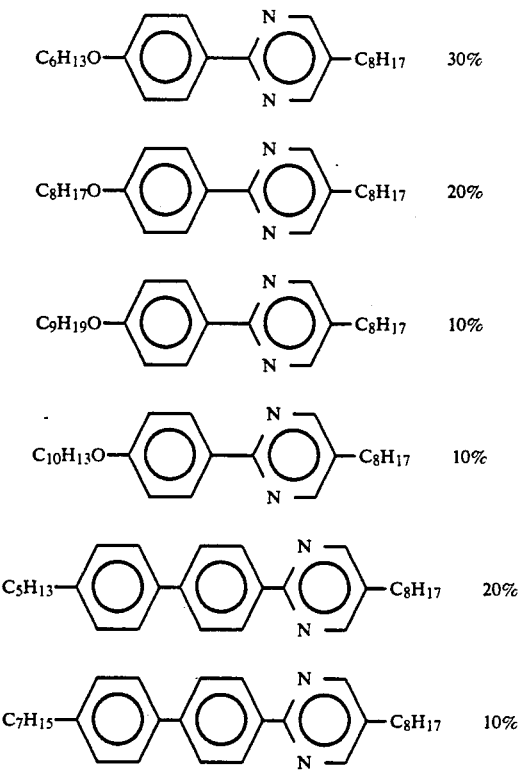

The above compounds were mixed to prepare a liquid crystal composition (A). This composition (A) exhibited the following phase transition values:
Cr 4 S$_C$ 65 S$_A$ 79 N 90 I.

To the above liquid crystal composition (A), (S) 1-methyl-2-keto-hexyl 4'-octyloxybiphenyl-4-ylcarboxylate prepared in Example 1 was added to prepare a ferroelectric liquid crystal composition (B) consisting of 95% of the liquid crystal composition (A) and 5% of the above compound. This composition (B) exhibited the following phase transition values:
S$_C$* 53 S$_A$* 78.4 N* 85.4 I.

The composition (B) was measured for Ps and tilt angle in the same manner as in Example 6. The results are shown in Table 2.

TABLE 2

| Temp. (°C.) | Ps (nc/cm$^2$) | Tilt Angle (°) |
|---|---|---|
| 48 | 1.8 | 11.0 |
| 43 | 2.4 | 13.5 |
| 38 | 2.8 | 14.8 |
| 33 | 3.0 | 15.5 |
| 25 | 3.3 | 16.3 |

The response time at 25° C. of the above ferroelectric liquid crystal composition (B) was 170 μsec.

COMPARATIVE EXAMPLE

A ferroelectric liquid crystal composition (C) consisting of 95% of the liquid crystal composition (A) as prepared in Example 8 and 5% of (R) 1-methylheptyl 4'-octyloxybiphenyl-4-ylcarboxylate was prepared.

This composition (C) exhibited the following phase transition values:

$S_C^*$ 51.3 $S_A$ 78.0 $N^*$ 84.0 I.

Ps, tilt angle, and response time at 25° C. of the ferroelectric liquid crystal composition (C) are shown in Table 8 along with those of the liquid crystal composition (B) of Example 8.

TABLE 3

|  | Composition | |
| --- | --- | --- |
|  | B | C |
| Ps (nC/cm²) | 3.3 | 1.4 |
| Tilt Angle (°) | 16.3 | 14.3 |
| Response Time (μsec) | 170 | 270 |

It can be seen from the results of Table 3 that the liquid crystal composition containing the compound of the present invention has a large spontaneous polarization (Ps) and short response time as compared with the liquid crystal composition containing the compound not falling within the scope of the present invention. That is, use of the compound of the present invention increases the spontaneous polarization of the resulting liquid crystal composition, and also shortens its response time.

EXAMPLE 9

A chiral nematic liquid crystal composition was prepared by adding 1% of (S) 4-(trans-4'-propylcyclohexyl)phenyl (1-pentanoyloxyethyl) ketone as prepared in Example 3 to a commercially available nematic liquid composition (trade name, ZLI-1132, produced by Merck & Co.). The chiral pitch length of the resulting chiral nematic liquid crystal composition is shown in Table 4.

TABLE 4

| Temp. (°C.) | Pitch |
| --- | --- |
| 20 | 7.0 |
| 30 | 7.2 |
| 40 | 7.3 |
| 50 | 7.5 |
| 60 | 7.8 |

It can be seen from the results of Table 4 that the chiral pitch length induced by the compound of the present invention is markedly short, and thus the compound of the present invention is most suitable for a display mode for which a high twist is required, such as super twisted nematic (STN) display devices.

What is claimed is:

1. An α-hydroxyketone derivative represented by the general formula (I):

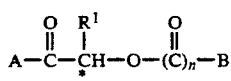

wherein:

A and B may be the same or different, and are independently a radical represented by the general formula (II):

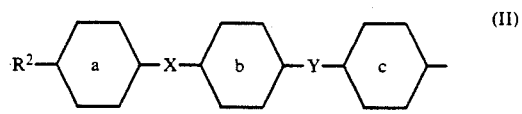

wherein $R^2$ is a saturated or unsaturated aliphatic hydrocarbon group having 1 to 16 carbon atoms, which may contain therein at least one ether bond, and may be substituted by at least one of a cyano group and a halogen atom,

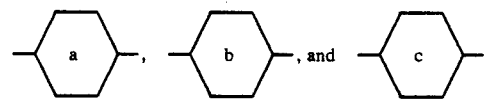

may be the same or different, and are independently a single bond,

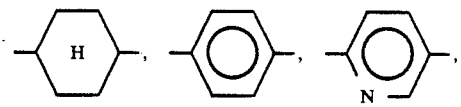

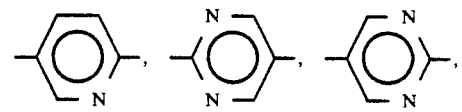

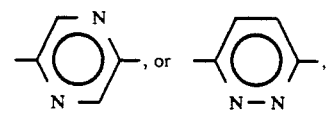

in which the radicals except for the single bond may be substituted by at least one of a cyano group and a halogen atom, and X and Y may be the same or different, and are independently a connecting bond selected from a single bond, —CH₂CH₂—,

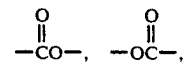

—CH₂O—, or —OCH₂—; or a saturated or unsaturated aliphatic hydrocarbon group having 1 to 16 carbon atoms, which may be substituted by a radical represented by the above general formula (II);
$R^1$ is an alkyl group having 1 to 5 carbon atoms, a phenyl group, or a cycloalkyl group;
n is 0 or 1; and
the asterisk (*) indicates an asymmetric carbon atom.

2. An α-hydroxyketone derivative as claimed in claim 1 wherein A is a radical selected from:

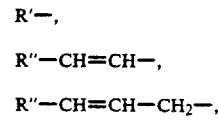

-continued
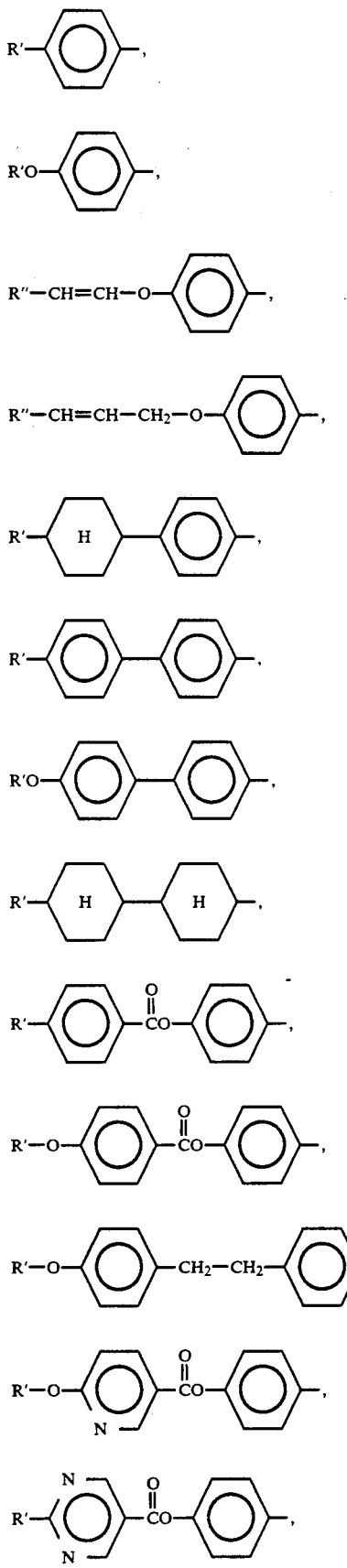
-continued
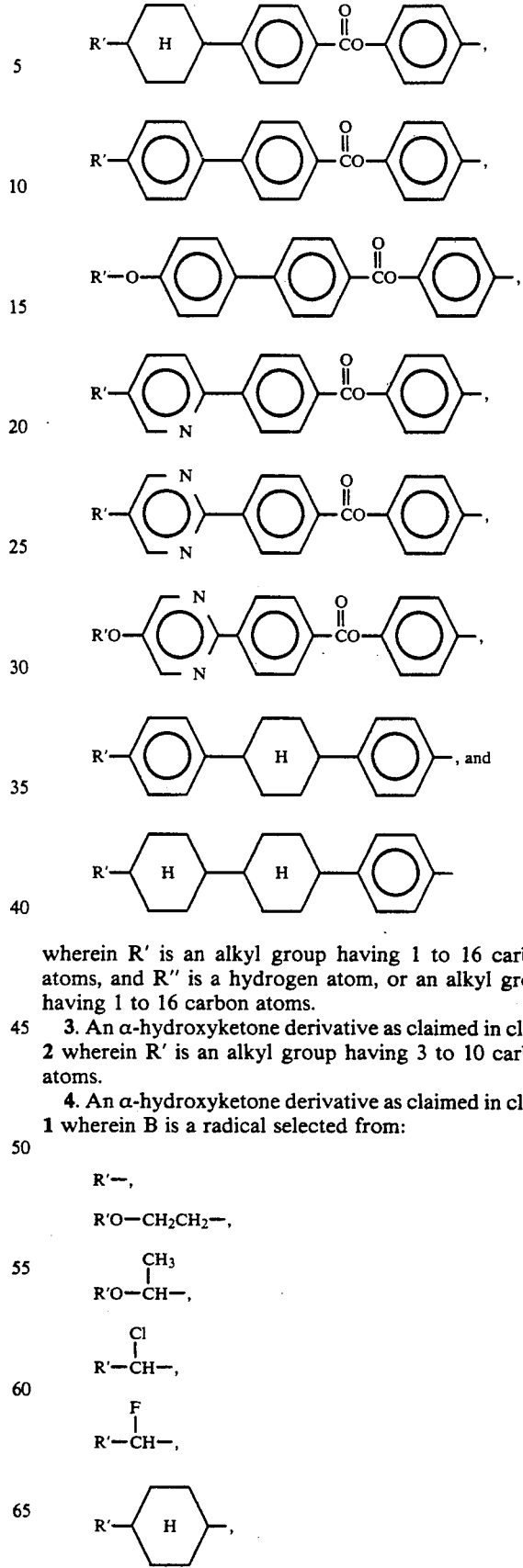
wherein R' is an alkyl group having 1 to 16 carbon atoms, and R" is a hydrogen atom, or an alkyl group having 1 to 16 carbon atoms.
3. An α-hydroxyketone derivative as claimed in claim 2 wherein R' is an alkyl group having 3 to 10 carbon atoms.
4. An α-hydroxyketone derivative as claimed in claim 1 wherein B is a radical selected from:

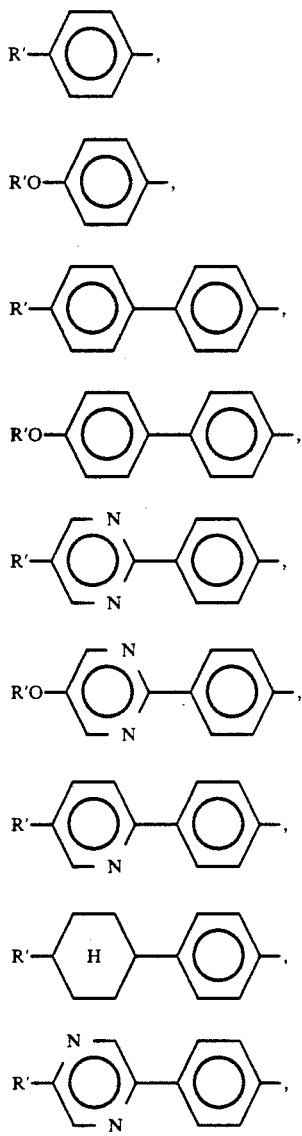

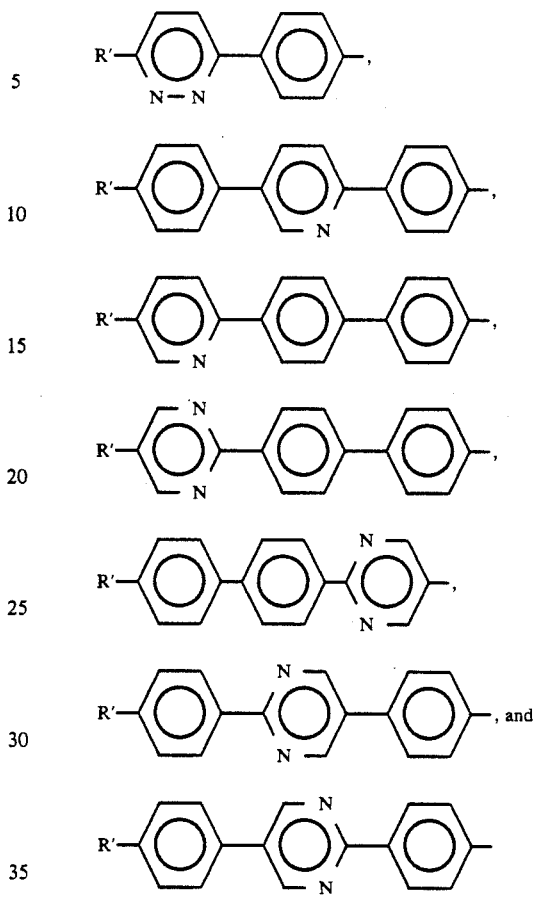

wherein R' is an alkyl group having 1 to 16 carbon atoms.

5. An α-hydroxyketone derivative as claimed in claim 4 wherein R' is an alkyl group having 3 to 10 carbon atoms.

6. An α-hydroxyketone derivative as claimed in claim 1 wherein $R^1$ is a methyl group, an isopropyl group, or a phenyl group.

7. An α-hydroxyketone derivative as claimed in claim 1, as represented by the following general formula:

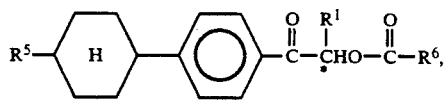

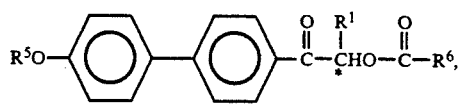

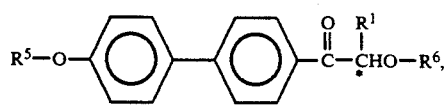

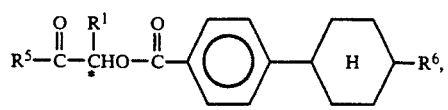

-continued

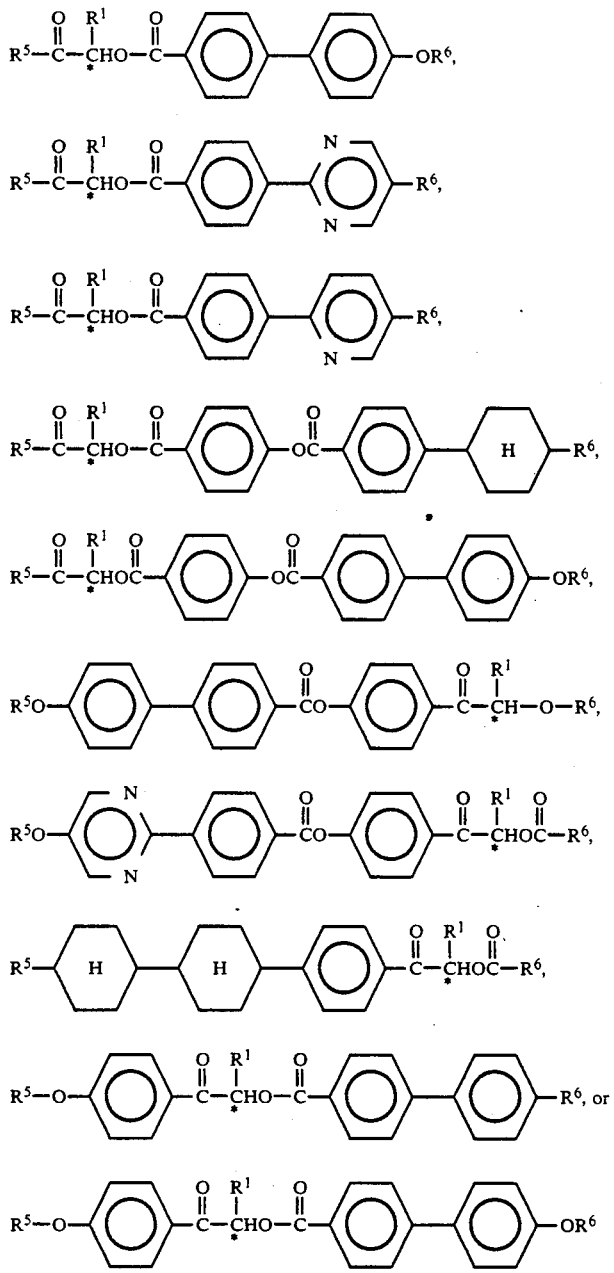

wherein R¹ is an alkyl group having 1 to 5 carbon atoms, a phenyl group, or a cyclohexyl group, R⁵ is an alkyl group having 1 to 15 carbon atoms, an alkenyl group having 1 to 15 carbon atoms, or an alkynyl group having 1 to 15 carbon atoms, and R⁶ is an alkyl group having 1 to 15 carbon atoms.

8. A liquid crystal composition containing at least two components, at least one of which is an α-hydroxyketone derivative represented by the general formula (I):

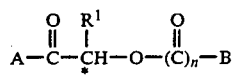 (I)

wherein:

A and B may be the same or different, and are independently a radical represented by the general formula (II):

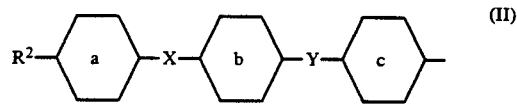 (II)

wherein R² is a saturated or unsaturated aliphatic hydrocarbons having 1 to 16 carbon atoms, which may contain therein at least one ether bond, and may be substituted by at least one of a cyano group and a halogen atom,

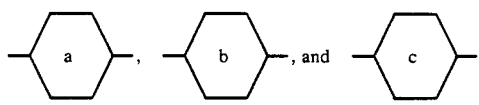

may be the same or different, and are independently a single bond,

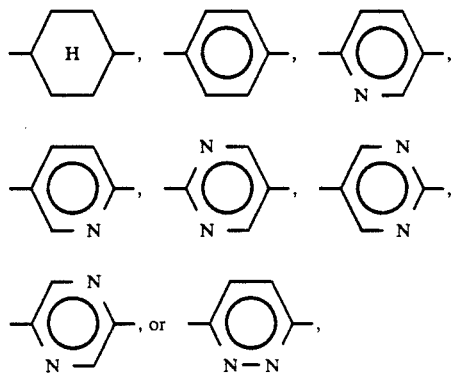

in which the radicals except for the single bond may be substituted by at least one of a cyano group and a halogen atom, and X and Y may be the same or different, and are independently a connecting bond selected from a single bond, —CH₂CH₂—,

—CH₂O—, or —OCH₂—; or a saturated or unsaturated aliphatic hydrocarbon group having 1 to 16 carbon atoms, which may be substituted by a radical represented by the above general formula (II);

$R^1$ is an alkyl group having 1 to 5 carbon atoms, a phenyl group, or a cyclohexyl group;

n is 0 or 1; and the asterisk (*) indicates an asymmetric carbon atom.

9. A liquid crystal composition as claimed in claim 8, which is a chiral smectic liquid crystal composition comprising:

a base material comprising at least one liquid crystal compound having a non-chiral, tilted smectic phase; and at least one α-hydroxyketone derivative represented by the general formula (I).

10. A liquid crystal composition as claimed in claim 9 wherein the base material comprises at least one liquid crystal compound having an Sc phase.

11. A liquid crystal composition as claimed in claim 9 wherein the amount of the α-hydroxyketone derivative used is 1 to 40% by weight based on the total weight of the composition.

12. A liquid crystal composition as claimed in claim 8, which is a chiral nematic liquid crystal composition comprising:

at least one nematic liquid crystal compound; and at least one α-hydroxyketone derivative represented by the general formula (I).

13. A liquid crystal composition as claimed in claim 12 wherein the amount of the α-hydroxyketone derivative used is 0.01 to 5% by weight based on the total weight of the composition.

14. A liquid crystal device comprising the liquid crystal composition as claimed in claim 8.

* * * * *